(12) United States Patent
Yeung et al.

(10) Patent No.: US 8,178,523 B2
(45) Date of Patent: *May 15, 2012

(54) COMPOUNDS FOR THE TREATMENT OF HEPATITIS C

(75) Inventors: Kap-Sun Yeung, Madison, CT (US); Ying Han, Cheshire, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/922,722

(22) PCT Filed: Mar. 25, 2009

(86) PCT No.: PCT/US2009/038186
§ 371 (c)(1),
(2), (4) Date: Sep. 29, 2010

(87) PCT Pub. No.: WO2009/120745
PCT Pub. Date: Oct. 1, 2009

(65) Prior Publication Data
US 2011/0020275 A1  Jan. 27, 2011

Related U.S. Application Data

(60) Provisional application No. 61/039,976, filed on Mar. 27, 2008.

(51) Int. Cl.
A61P 31/12  (2006.01)
A61K 31/55  (2006.01)
C07D 487/04 (2006.01)

(52) U.S. Cl. .................. 514/214.01; 540/576
(58) Field of Classification Search ............. 514/214.01; 540/576
See application file for complete search history.

(56) References Cited

U.S. PATENT DOCUMENTS

| | | | |
|---|---|---|---|
| 7,153,848 B2 | 12/2006 | Hudyma et al. | |
| 7,348,425 B2 | 3/2008 | Hudyma et al. | |
| 7,399,758 B2 | 7/2008 | Meanwell et al. | |
| 7,452,876 B2 | 11/2008 | Yeung et al. | |
| 7,456,165 B2 | 11/2008 | Bergstrom et al. | |
| 7,456,166 B2 | 11/2008 | Bender et al. | |
| 7,456,167 B2 | 11/2008 | Bergstrom | |
| 7,473,688 B2 | 1/2009 | Bergstrom et al. | |
| 7,485,633 B2 | 2/2009 | Meanwell et al. | |
| 7,517,872 B2 | 4/2009 | Nickel et al. | |
| 7,521,441 B2 | 4/2009 | Gentles et al. | |
| 7,521,442 B2 | 4/2009 | Gentles et al. | |
| 7,521,443 B2 | 4/2009 | Bender et al. | |
| 7,521,444 B2 | 4/2009 | Bender et al. | |
| 7,538,102 B2 | 5/2009 | Yeung et al. | |
| 7,538,103 B2 | 5/2009 | Hewawasam et al. | |
| 7,541,351 B2 | 6/2009 | Bender et al. | |
| 7,541,353 B2 | 6/2009 | Gentles et al. | |
| 7,547,690 B2 | 6/2009 | Gentles et al. | |
| 2008/0221090 A1 | 9/2008 | Yeung et al. | |
| 2009/0018163 A1 | 1/2009 | Schmitz et al. | |
| 2009/0130057 A1 | 5/2009 | Hewawasam et al. | |
| 2010/0216774 A1 | 8/2010 | Bender et al. | |

FOREIGN PATENT DOCUMENTS

| | | |
|---|---|---|
| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/033032 | 3/2007 |
| WO | WO 2007/092888 | 8/2007 |
| WO | WO 2007/129119 | 11/2007 |
| WO | WO 2009/067108 | 5/2009 |
| WO | WO 2009/067392 | 5/2009 |
| WO | WO 2009/120733 | 10/2009 |

*Primary Examiner* — Brenda Coleman
(74) *Attorney, Agent, or Firm* — James Epperson

(57) ABSTRACT

The disclosure provides compounds of formula (I), including their salts, as well as compositions and methods of using the compounds. The compounds have activity against hepatitis C virus (HCV) and may be useful in treating those infected with HCV.

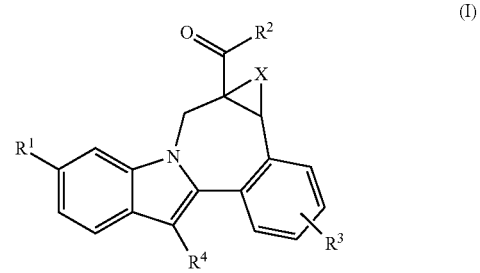

15 Claims, No Drawings

COMPOUNDS FOR THE TREATMENT OF HEPATITIS C

CROSS-REFERENCE TO RELATED APPLICATIONS

This application claims the benefit of U.S. provisional application Ser. No. 61/039,976 filed Mar. 27, 2008.

BACKGROUND OF THE INVENTION

The disclosure generally relates to the novel compounds of formula I, including their salts, which have activity against hepatitis C virus (HCV) and may be useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop further effective compounds for the treatment of HCV infection.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy; target selectivity, solubility, safety profiles, or bioavailability.

HCV NS5B inhibitors have been disclosed in U.S. Pat. Nos. 7,473,688 and 7,399,758.

DESCRIPTION OF THE INVENTION

The invention encompasses compounds of formula I, including pharmaceutically acceptable salts, and compositions and methods of treatment using these compounds.

One aspect of the invention is a compound of formula I

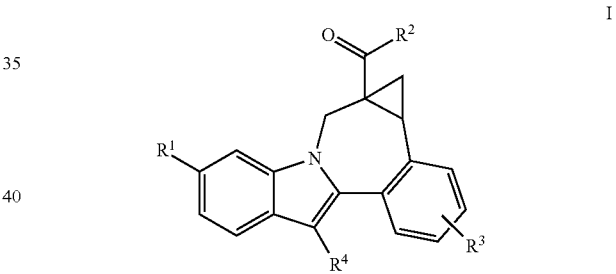

where:
$R^1$ is $CO_2R^5$ or $CONR^6R^7$;
$R^2$ is piperidine substituted with 1 $Ar^1$;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^8)(R^9)NSO_2$, or $(R^{10})SO_2$;
$R^7$ is hydrogen or alkyl;
$R^8$ is hydrogen or alkyl;
$R^9$ is hydrogen or alkyl;
$R^{10}$ is azetidinyl, pyrrolidinyl, piperidinyl, piperazinyl, N-(alkyl)piperazinyl, morpholinyl, thiomorpholinyl, homopiperidinyl, or homomorpholinyl;
$Ar^1$ is pyrrolyl, thienyl, furanyl, pyrazolyl, isoxazolyl, isothiazolyl, imidazolyl, oxazolyl, thiazolyl, triazolyl, oxadiazolyl, thiadiazolyl, indolyl, oxindolyl, benzofuranyl, benzothioenyl, indazolyl, benzisoxazolyl, benzisothiazolyl, benzimidazolyl, benzimidazolonyl, benzoxazolyl, benzthiazolyl, or benztriazolyl, and is substituted with 0-2 substituents selected from halo, alkyl, cycloalkyl, alkoxy, amino, alkylamino, dialkylamino, carboxy, alkoxycarbonyl, furanyl, and phenyl where phenyl is substituted with 0-2 halo, alkyl, or alkoxy substituents; and X is absent, a bond, or methylene;

or a pharmaceutically acceptable salt thereof.

Another aspect of the invention is a compound of formula I where $R^1$ is $CONR^6R^7$; $R^2$ is piperidine substituted with 1 $Ar^1$; $R^3$ is alkoxy; $R^4$ is cycloalkyl; $R^6$ is alkyl$SO_2$ or $(R^8)(R^9)NSO_2$; $R^7$ is hydrogen; $R^8$ is alkyl; $R^9$ is alkyl; $Ar^1$ is pyrazolyl, oxazolyl, thiazolyl, triazolyl, oxadiazolyl, thiadiazolyl, indolyl, benzofuranyl, benzisoxazolyl, benzimidazolyl, benzimidazolonyl, or benzoxazolyl, and is substituted with 0-2 substituents selected from halo, alkyl, amino, alkoxycarbonyl, furanyl, and phenyl where phenyl is substituted with 0-2 halo or alkoxy substituents; and X is a bond or methylene; or a pharmaceutically acceptable salt thereof.

Another aspect of the invention is a compound of formula I where $R^1$ is $CONR^6R^7$; $R^2$ is piperidine substituted with 1 $Ar^1$; $R^3$ is methoxy; $R^4$ is cyclohexyl; $R^6$ is isopropyl$SO_2$ or (dimethylamino)$SO_2$; $R^7$ is hydrogen; $Ar^1$ is (furanyl)pyrazolyl, (ethylcarboxy)oxazolyl, thiazolyl, (methyl)triazolyl, (dimethyl)triazolyl, (methyl)oxadiazolyl, (ethyl)oxadiazolyl, (propyl)oxadiazolyl, (isopropyl)oxadiazolyl, (phenyl)oxadiazolyl, (amino)thiadiazolyl, indolyl, benzofuranyl, fluorobenzisoxazolyl, (methyl)benzimidazolyl, (phenyl)pyrazolyl, (chlorophenyl)pyrazolyl, (methoxyphenyl)pyrazolyl, benzimidazolonyl, or benzoxazolyl; and X is a bond or methylene; or a pharmaceutically acceptable salt thereof.

Another aspect of the invention is a compound of formula I where $R^1$ is $CONR^6R^7$; $R^6$ is alkyl$SO_2$, cycloalkyl$SO_2$, haloalkyl$SO_2$, $(R^8)(R^9)NSO_2$, or $(R^{10})SO_2$; and $R^7$ is hydrogen.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^8)(R^9)NSO_2$ or $(R^{10})SO_2$.

Another aspect of the invention is a compound of formula I where $Ar^1$ is pyrazolyl, thiazolyl, triazolyl, oxadiazolyl, thiadiazolyl, benzisoxazolyl, benzimidazolyl, benzimidazolonyl, or benzoxazolyl, and is substituted with 0-2 substituents selected from halo, alkyl, amino, alkylamino, dialkylamino, carboxy, alkoxycarbonyl, furanyl, and phenyl where phenyl is substituted with 0-2 halo, alkyl, or alkoxy substituents.

Another aspect of the invention is a compound of formula I where $Ar^1$ is pyrazolyl, oxazolyl, thiazolyl, triazolyl, oxadiazolyl, thiadiazolyl, indolyl, benzofuranyl, benzisoxazolyl, benzimidazolyl, benzimidazolonyl, or benzoxazolyl, and is substituted with 0-2 substituents selected from halo, alkyl, amino, alkoxycarbonyl, furanyl, and phenyl where phenyl is substituted with 0-2 halo or alkoxy, substituents Another aspect of the invention is a compound of formula I where $Ar^1$ is (furanyl)pyrazolyl, (ethylcarboxy)oxazolyl, thiazolyl, (methyl)triazolyl, (dimethyl)triazolyl, (methyl)oxadiazolyl, (ethyl)oxadiazolyl, (propyl)oxadiazolyl, (isopropyl)oxadiazolyl, (phenyl)oxadiazolyl, (amino)thiadiazolyl, indolyl, benzofuranyl, fluorobenzisoxazolyl, (methyl)benzimidazolyl, (phenyl)pyrazolyl, (chlorophenyl)pyrazolyl, (methoxyphenyl)pyrazolyl, or benzimidazolonyl, benzoxazolyl Another aspect of the invention is a compound of formula I where X is absent.

Another aspect of the invention is a compound of formula I where X is a bond.

Another aspect of the invention is a compound of formula I where X is methylene.

Another aspect of the invention is a compound of formula I according to the following stereochemistry.

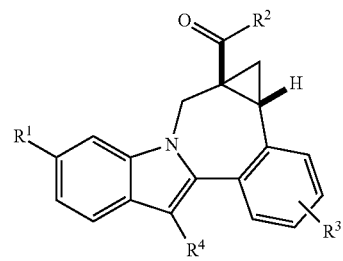

Another aspect of the invention is a compound of formula I according to the following stereochemistry.

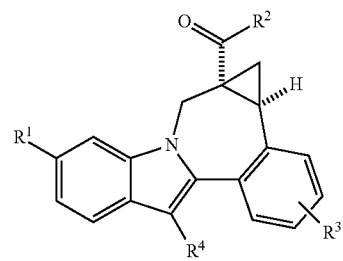

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $Ar^1$, and X, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments unless indicated.

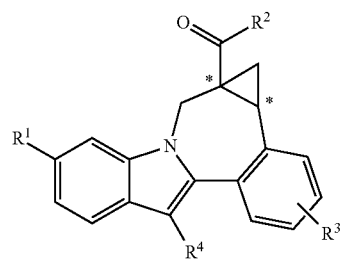

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Scheme 1 shows how a piperidine amide can be made on the core structure. Methods of making substituted piperidines are known in the art and some examples are described below.

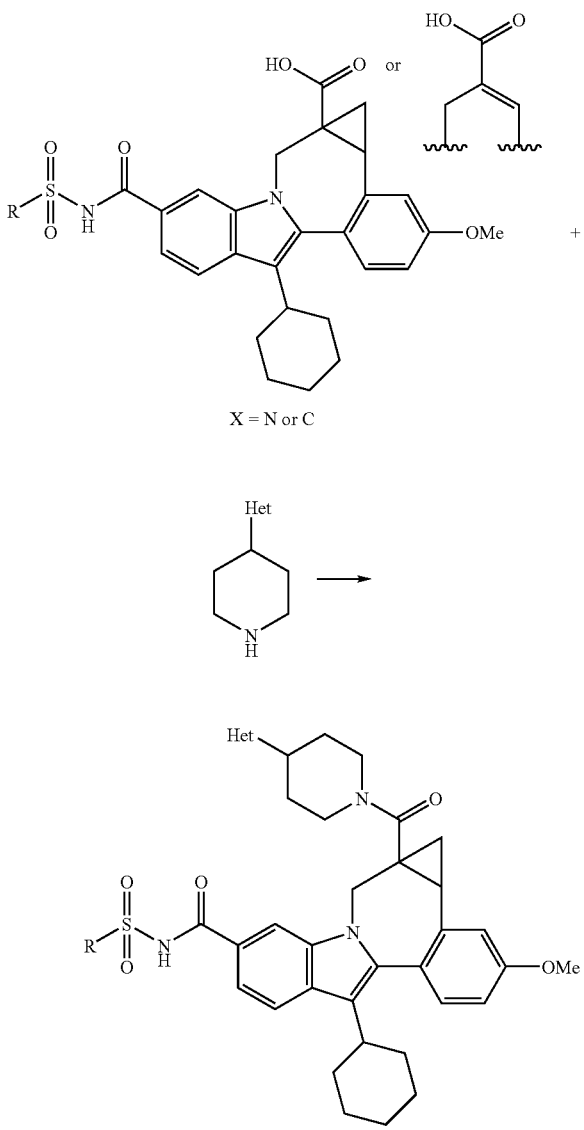

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM MTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using two sequential chromatography steps: Heparin sepharose CL-6B and polyU sepharose 4B (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Corning 3600). The assay buffer is composed of 20 mM Hepes, pH 7.5, 2.5 mM KCl, 2.5 mM MgCl2, 1 mM DTT, 1.6 U RNAse inhibitor (Promega N2515), 0.01 mg/ml BSA (Sigma B6917), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 mg/μl beads. Order of addition in the assay: enzyme (1.75 nM) was added to diluted compound followed by the addition of a mixture of template (0.36 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. The HCV FRET screening assay was performed in 96-well cell culture plates. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 μM final from a 2 mM stock.

To prepare plates, HCV replicon cells, with or without a *Renilla* luciferase reporter gene, were trypsinized and plated in a 96-well plate with titrated test compounds added in columns 3 through 12; columns 1 and 2 contained a control compound (HCV control inhibitor), and the bottom row contained cells with DMSO only. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added to measure cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for up to 20 cycles and the plate read in a kinetic mode. Typically, the signal to noise using an endpoint analysis after the reads was at least three-fold. Alternatively, after Alamar blue reading, plates were rinsed with PBS, then used for luciferase assay using the Promega Dual-Glo Luciferase Assay System or the Promega EnduRen Live Cell Substrate assay.

Compound analysis was performed by quantification of the relative HCV replicon inhibition and the relative cytotoxicity values. To calculate cytotoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV control inhibitor at the end of the assay period. These numbers were similar to those obtained from naïve Huh-7 cells. The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values were calculated as the concentration which caused a 50% reduction in FRET or luciferase activity. The two numbers generated for the compound plate, percent cytotoxicity and percent activity, were used to determine compounds of interest for further analysis.

Representative data for compounds are reported in Table 1.
TABLE 1
| Structure | IC$_{50}$ | EC$_{50}$ |
|---|---|---|
| 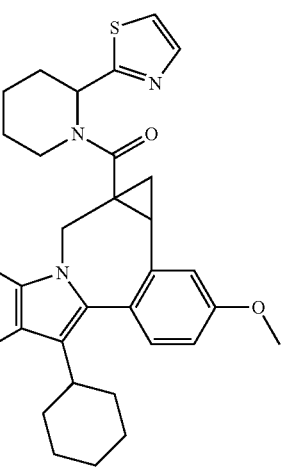 | 0.07 | 0.29 |
| 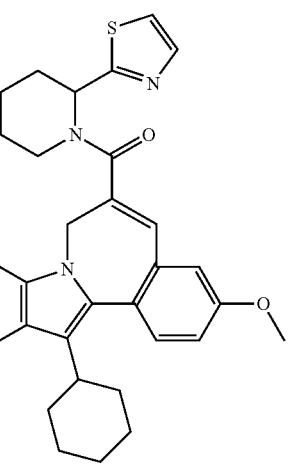 | 0.10 | 0.46 |
| 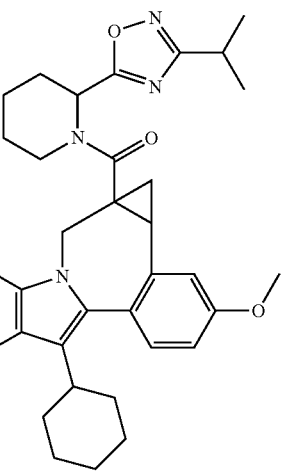 | B | B |

TABLE 1-continued
| Structure | IC$_{50}$ | EC$_{50}$ |
|---|---|---|
| 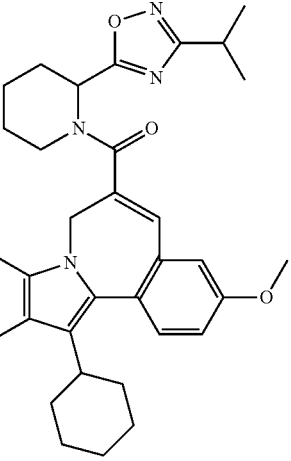 | 0.15 | 1.00 |
| 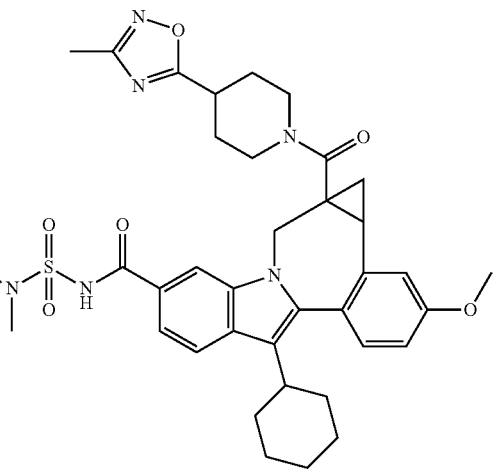 | 0.03 | 0.09 |
| 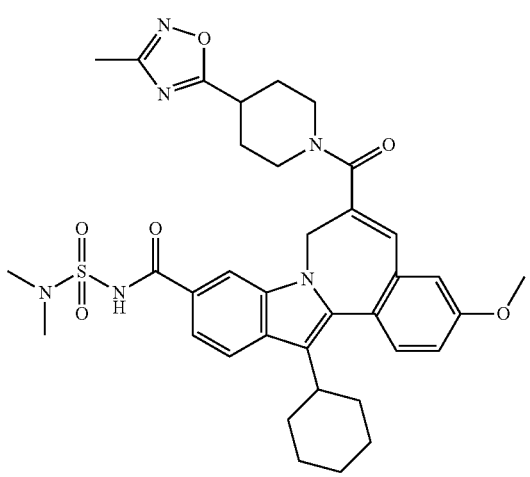 | 0.09 | 0.23 |

TABLE 1-continued

| Structure | IC₅₀ | EC₅₀ |
|---|---|---|
| | B | B |
| | B | B |
| 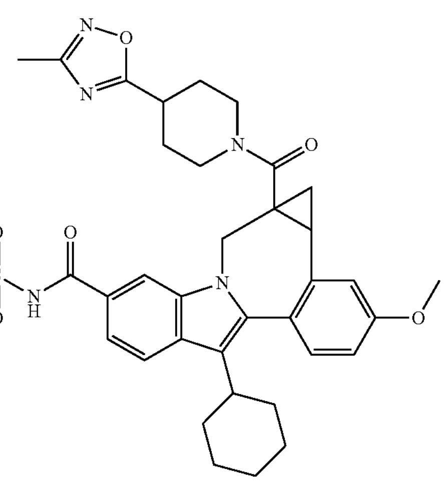 | 0.03 | 0.10 |

TABLE 1-continued
| Structure | IC$_{50}$ | EC$_{50}$ |
|---|---|---|
| 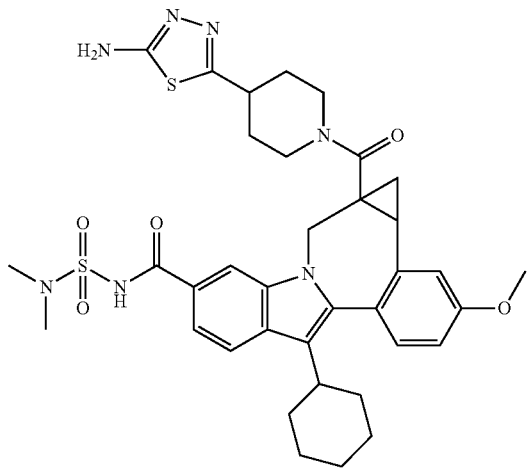 | 0.06 | 0.19 |
| 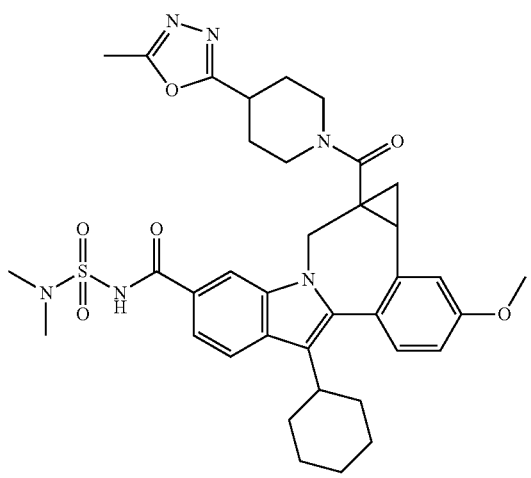 | 0.02 | 0.05 |
| 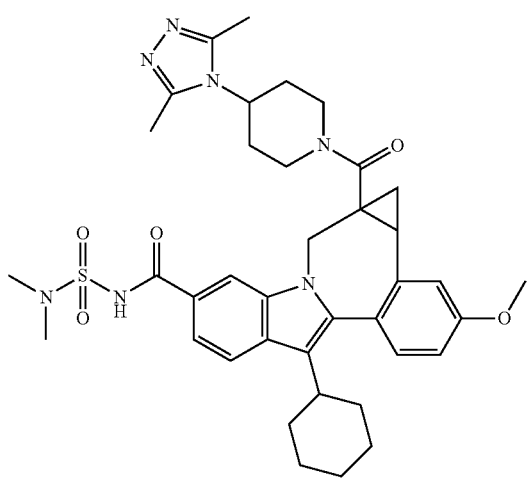 | B | B |

TABLE 1-continued
| Structure | IC$_{50}$ | EC$_{50}$ |
|---|---|---|
| 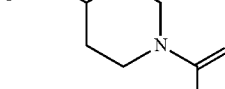 | 0.07 | 0.11 |
| 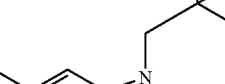 Chiral | 0.03 | 0.03 |
| 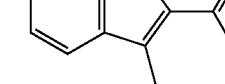 | B | B |

TABLE 1-continued

| Structure | IC$_{50}$ | EC$_{50}$ |
|---|---|---|
| | B | B |
| | B | B |
| 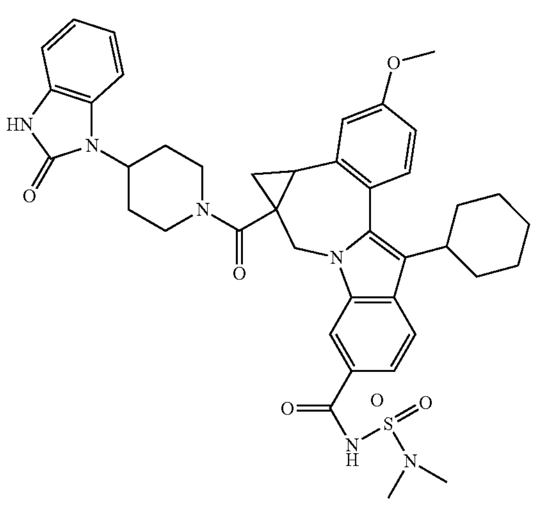 | 0.11 | 0.43 |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
|---|---|---|
| 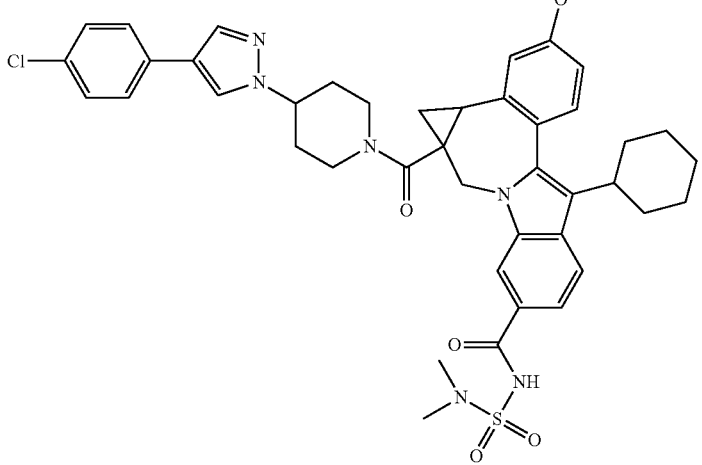 | B | B |
| 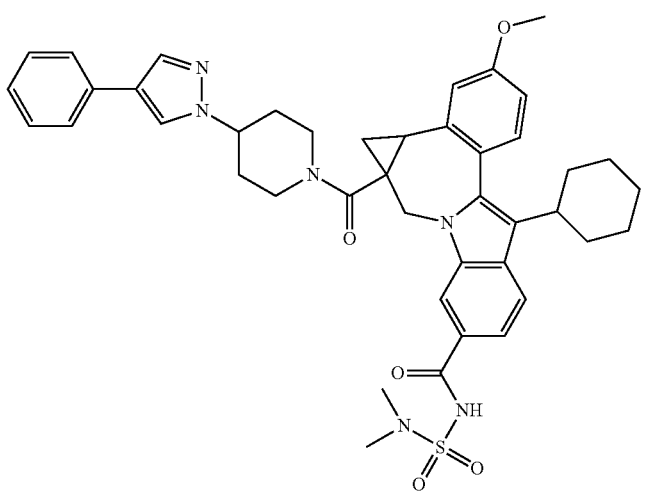 | B | B |
| 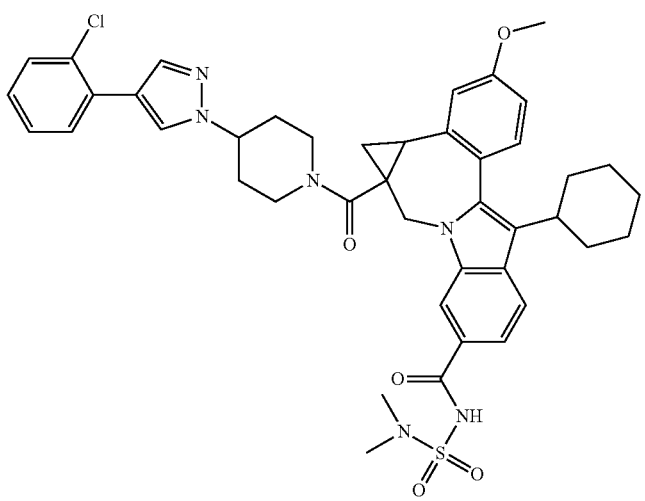 | B | B |

TABLE 1-continued

| Structure | IC$_{50}$ | EC$_{50}$ |
|---|---|---|
| | B | B |
| | B | B |
| | B | B |

TABLE 1-continued
| Structure | IC$_{50}$ | EC$_{50}$ |
|---|---|---|
| 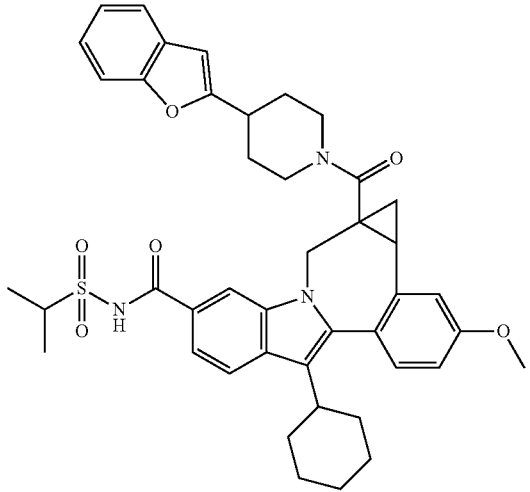 | B | A |
| 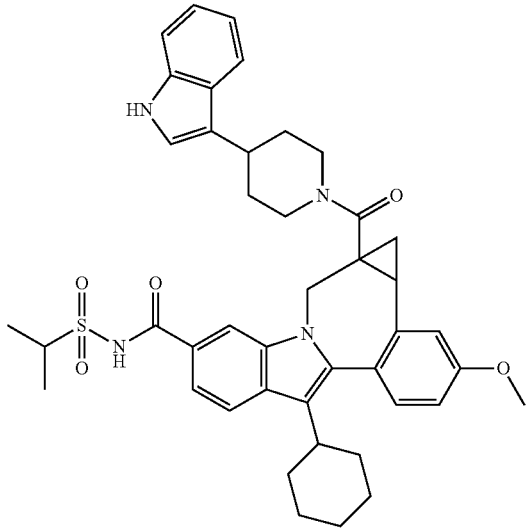 | B | B |
| 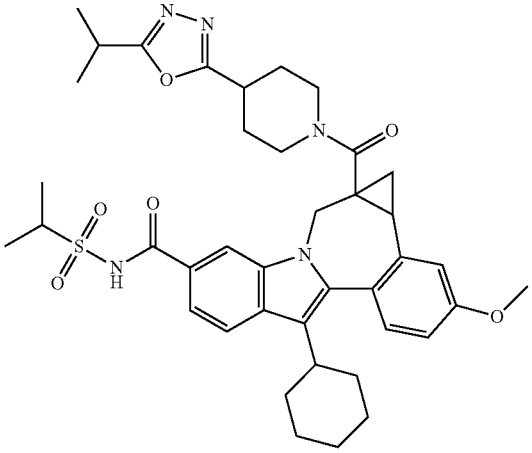 | B | B |
A > 0.5 μM; B 0.002 μM-0.5 μM; C < 0.02 μM but an exact value was not determined;

Pharmaceutical Compositions and Methods of Treatment

The compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of hepatitis C.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, and an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection. A therapeutically effective amount is that which is needed to provide a meaningful patient benefit.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

General Procedure. To a mixture of the corresponding acid (30 mg), heteroaryl-substituted piperidine (1.5 equiv.) and 2-(1H-benzo[d][1,2,3]triazol-1-yl)-1,1,3,3-tetramethylisouronium tetrafluoroborate (2 equiv.) in DMF (1 ml) at r.t. under N$_2$ was added N,N-diisopropylethylamine (3 equiv.). The mixture was stirred at r.t. for about 17 hr. The mixture was then diluted with MeOH and purified by Shimadzu-VP preparative reverse phase HPLC.

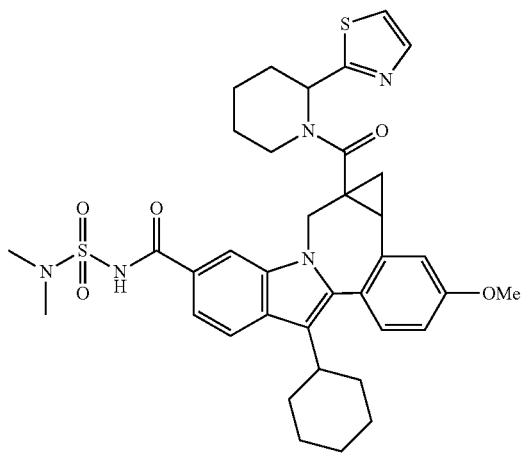

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[2-(2-thiazolyl)-1-piperidinyl]carbonyl]-, Prepared as a TFA salt from the coupling between the racemic acid, cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, and 2-(piperidin-2-yl)thiazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 9.59-10.15 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=702.41, HPLC R$_t$=1.942 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)$^+$=702.52, HPLC R$_t$=1.492 min. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 min, Stop time=20 min, Flow Rate=1 ml/min, Column: Waters Sunfire C-18, 4.6×150 mm, 3.5 um, R$_t$=12.47 min; Column: Waters Xbridge Phenyl column 4.6×150 mm, 3.5 um, R$_t$=10.93 min.

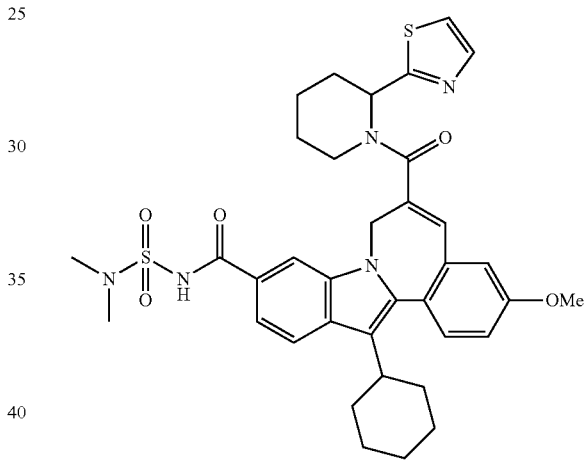

7H-indolo[2,1-a][2]benzazepine-10-carboxamide, 13-cyclohexyl-N-[(dimethylamino)sulfonyl]-3-methoxy-6-[[2-(2-thiazolyl)-1-piperidinyl]carbonyl]-, Prepared as a TFA salt from the coupling between the unsaturated acid, 7H-indolo[2,1-a][2]benzazepine-6-carboxylic acid, 13-cyclohexyl-10-[[[(dimethylamino)sulfonyl]amino]carbonyl]-3-methoxy-, and 2-(piperidin-2-yl)thiazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 10.15-10.76 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=688.38, HPLC R$_t$=1.957 min. HPLC method: Solvent A=5% MeCN-95% H$_2$O-10 mM NH$_4$OAc, Solvent B=95% MeCN-5% H₂O-10 mM NH₄OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)⁺=688.49, HPLC R$_t$=1.530 min. Analytical HPLC method: Solvent A=5% MeCN-95% H₂O-0.1% TFA, Solvent B=95% MeCN-5% H₂O-0.1% TFA, Start % B=10, Final % B=100, Gradient time=10 min, Stop time=20 min, Flow Rate=1 ml/min, Column: Waters Sunfire C-18, 4.6×150 mm, 3.5 um, R$_t$=12.29 min; Column: Waters Xbridge Phenyl column 4.6×150 mm, 3.5 um, R$_t$=10.94 min.

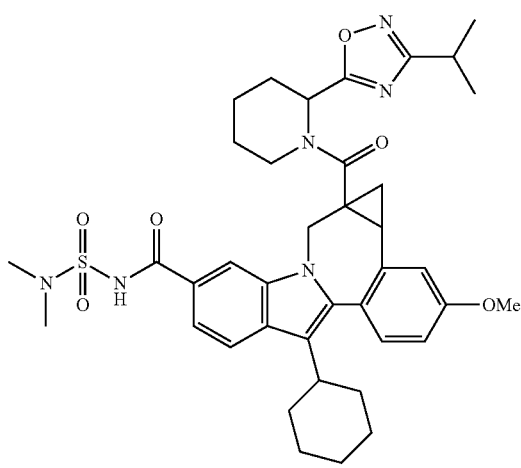

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[2-[3-(1-methylethyl)-1,2,4-oxadiazol-5-yl]-1-piperidinyl]carbonyl]-. Prepared as a TFA salt from the coupling between the racemic acid and 3-isopropyl-5-(piperidin-2-yl)-1,2,4-oxadiazole in a similar manner as described above. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 10.44-11.29 min. (UV detection at 220 nm). LC/MS were performed by using Shimadzu-VP instrument with UV detection at 220 nm and Waters Micromass. HPLC method: Solvent A=10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)⁺=729.46, HPLC R$_t$=2.027 min. HPLC method: Solvent A=5% MeCN-95% H₂O-10 mM NH₄OAc, Solvent B=95% MeCN-5% H₂O-10 mM NH₄OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)⁺=729.50, HPLC R$_t$=1.663 min. Analytical HPLC method: Solvent A=5% MeCN-95% H₂O-0.1% TFA, Solvent B=95% MeCN-5% H₂O-0.1% TFA, Start % B=10, Final % B=100, Gradient time=10 min, Stop time=20 min, Flow Rate=1 ml/min, Column: Waters Xbridge Phenyl column 4.6×150 mm, 3.5 um, R$_t$=11.35 min.

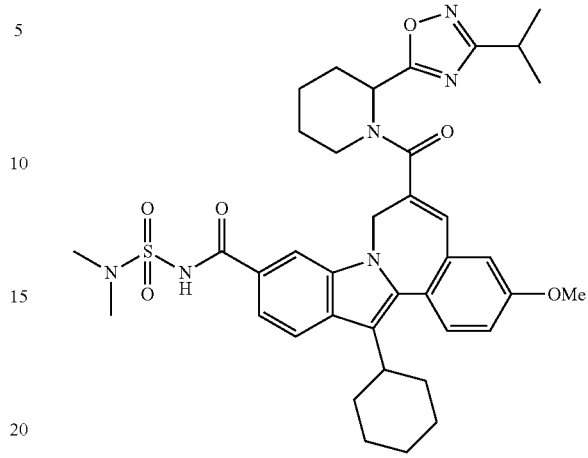

7H-indolo[2,1-a][2]benzazepine-10-carboxamide, 13-cyclohexyl-N-[(dimethylamino)sulfonyl]-3-methoxy-6-[[2-[3-(1-methylethyl)-1,2,4-oxadiazol-5-yl]-1-piperidinyl]carbonyl]-. Prepared as a TFA salt from the coupling between the unsaturated acid and 3-isopropyl-5-(piperidin-2-yl)-1,2,4-oxadiazole in a similar manner as described above. Purification by Shimadzu-VP preparative reverse phase HPLC using the separation method: Solvent A=10% MeOH-90% H₂O-0.1% TFA, Solvent B=90% MeOH-10% H₂O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 10.59-11.20 min. (UV detection at 220 nm). ¹H NMR (500 MHz, CD₃OD) δ 8.15 (broad s, 1H), 7.91 (broad s, 1H), 7.59 (broad s, 1H), 7.57 (d, J=8.5, 1H), 7.16 (broad d, 1H), 7.06 (broad s, 2H), 5.20 (broad s, 1H), 4.42 (broad s, 1H), 3.93 (s, 3H), 3.17 (m, 1H), 3.09 (broad s, 1H), 3.03 (s, 6H), 2.88 (broad m, 2H), 2.35 (broad s, 1H), 2.21-1.88 (overlapping broad in, 5H), 1.86-1.67 (overlapping broad in, 3H), 1.67-1.16 (overlapping broad m, 8H), 1.32 (s, 6H). LC/MS were performed by using Shimadzu-VP instrument with UV detection at 220 nm and Waters Micromass. HPLC method: Solvent A 10% MeOH-90% H₂O-0.1% TFA, Solvent B=90% MeOH-10% H₂O-0.1% TFA, Start % B=0, Final % B=100, Gradient time=2 min, Stop time=3 min, Flow Rate=5 ml/min, Column: Xterra MS C18 S7 3.0×50 mm; (ES+) (M+H)⁺=715.41, HPLC R$_t$=2.025 min. HPLC method: Solvent A=5% MeCN-95% H₂O-10 mM NH₄OAc, Solvent B=95% MeCN-5% H₂O-10 mM NH₄OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)⁺ =715.45, HPLC R$_t$=1.657 min. Analytical HPLC method: Solvent A=5% MeCN-95% H₂O-0.1% TFA, Solvent B=95% MeCN-5% H₂O-0.1% TFA, Start % B=10, Final % B=100, Gradient time=10 min, Stop time=20 min, Flow Rate=1 ml/min, Waters Sunfire C-18, 4.6×150 mm, 3.5 um, R$_t$=13.06 mM; Column: Waters Xbridge Phenyl column 4.6×150 mm, 3.5 um, R$_t$=11.38 min.

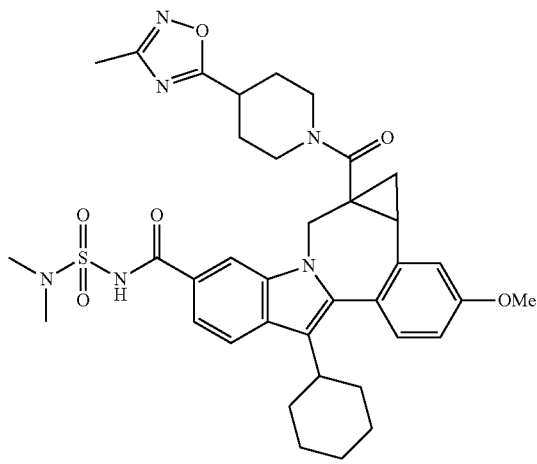
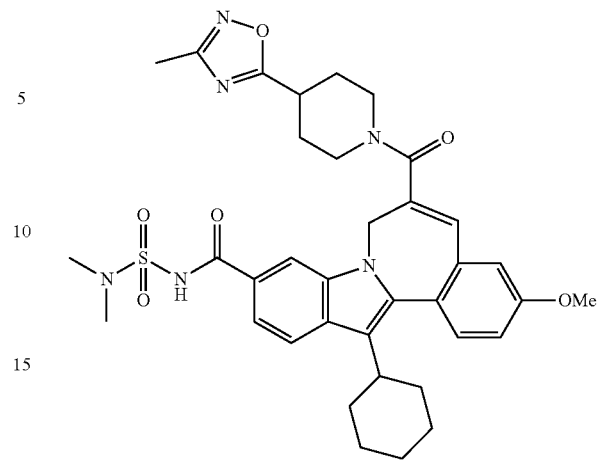

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(3-methyl-1,2,4-oxadiazol-5-yl)-1-piperidinyl]carbonyl]-, Prepared as a TFA salt from the coupling between the racemic acid and 3-methyl-5-(piperidin-4-yl)-1,2,4-oxadiazole in a similar manner as described above. Purification by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 9.37-9.97 min. (UV detection at 220 nm). $^1$H NMR (500 MHz, $CD_3OD$, as a mixture of two isomers in about 2:1 ratio) δ 8.10 (s, 0.5H), 7.96 (s, 1H), 7.91 (d, J=8.5, 0.5H), 7.85 (d, J=8.0, 1H), 7.62 (dd, J=8.5, 1.5, 0.5H), 7.52 (d, J=8.0, 1H), 7.324 (d, J=8.5, 0.5H), 7.315 (d, J=8.5, 1H), 7.20 (d, J=2, 1H), 7.18 (d, J=2, 0.5H), 7.02 (dd, J=8.5, 2.5, 1H), 7.00 (dd, 0.5H), 5.09 (broad d, J=15.5, 1H), 4.84 (d, 0.5H), 4.13 (d, J=15, 0.5H), 3.91 (s, 1.5H), 3.90 (s, 3H), 3.66 (d, J=15.5, 1H), 3.34-3.23 (overlapping m, 2.5H), 3.23-3.17 (overlapping m, 0.5H) 3.11-2.90 (overlapping in, 2.5H), 3.01 (s, 9H), 2.84 (m, 1H), 2.72 (broad m, 1H), 2.65 (broad m, 1H), 2.52 (dd, J=9.9, 6.3, 0.5H), 2.37 (s, 4.5H), 2.28-1.72 (broad overlapping m, 14H), 1.62 (broad d, 1.5H), 1.57-1.18 (broad overlapping m, 9H), 1.07 (dd, J=9.9, 6.0, 0.5H), 0.18 (t, J=6.0, 0.5H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Xterra MS C18 S7 3.0×50 mm; (ES+) m/z $(M+H)^+$=701.46, HPLC $R_t$=1.870 min. HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Stop time=3 min, Flow Rate=5 ml/min, Column: Phenomenex Lina C18 5 um 3.0×50 mm; (ES+) m/z $(M+H)^+$=701.46, HPLC $R_t$=1.390 min. Analytical HPLC were performed by using Shimadzu-VP instrument with UV detection at 254 nm and 256 nm. Analytical HPLC method: Solvent A=5% MeCN-95% $H_2O$-0.1% TFA, Solvent B=95% MeCN-5% $H_2O$-0.1% TFA, Start % B=10, Final % B=100, Gradient time=10 min, Stop time=20 min, Flow Rate=1 ml/min, Column: Waters Sunfire C-18, 4.6×150 mm, 3.5 um, $R_t$=11.66 mM; Column: Waters Xbridge Phenyl column 4.6×150 mm, 3.5 um, $R_t$=10.40 min.

7H-indolo[2,1-a][2]benzazepine-10-carboxamide, 13-cyclohexyl-N-[(dimethylamino)sulfonyl]-3-methoxy-6-[[4-(3-methyl-1,2,4-oxadiazol-5-yl)-1-piperidinyl]carbonyl]-. Prepared as a TFA salt from the coupling between the unsaturated acid and 3-methyl-5-(piperidin-4-yl)-1,2,4-oxadiazole in a similar manner as described above. Purification by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 9.48-10.08 min. (UV detection at 220 nm). $^1$H NMR (500 MHz, $CD_3OD$) δ 8.12 (s, 1H), 7.91 (d, J=8.5, 1H), 7.59 (dd, J=8.5, 1.5, 1H), 7.55 (d, J=8.5, 1H), 7.15 (dd, J=8.5, 2.5, 1H), 7.10 (s, 1H), 6.98 (s, 1H), 5.13 (broad in, 1H), 4.37 (broad m, 1H), 3.93 (s, 3H), 3.27-3.07 (overlapping in, 4H), 3.02 (s, 6H), 2.92-2.81 (overlapping in, 2H), 2.35 (s, 3H), 2.21-1.67 (overlapping broad m, 10H), 1.57-1.32 (overlapping broad m, 3H), 1.24 (broad m, 1H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Xterra MS C18 S7 3.0×50 mm; (ES+) m/z $(M+H)^+$=687.42, HPLC $R_t$=1.882 min. HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Stop time=3 min, Flow Rate=5 ml/min, Column: Phenomenex Lina C18 5 um 3.0×50 mm; (ES+) m/z $(M+H)^+$=687.40, HPLC $R_t$=1.440 min. Analytical HPLC were performed by using Shimadzu-VP instrument with UV detection at 254 nm and 256 nm. Analytical HPLC method: Solvent A=5% MeCN-95% $H_2O$-0.1% TFA, Solvent B=95% MeCN-5% $H_2O$-0.1% TFA, Start % B=10, Final % B=100, Gradient time=10 min, Stop time=20 min, Flow Rate=1 ml/min, Column: Waters Sunfire C-18, 4.6×150 mm, 3.5 um, $R_t$=11.62 min; Column: Waters Xbridge Phenyl column 4.6×150 mm, 3.5 um, $R_t$=10.46 min.

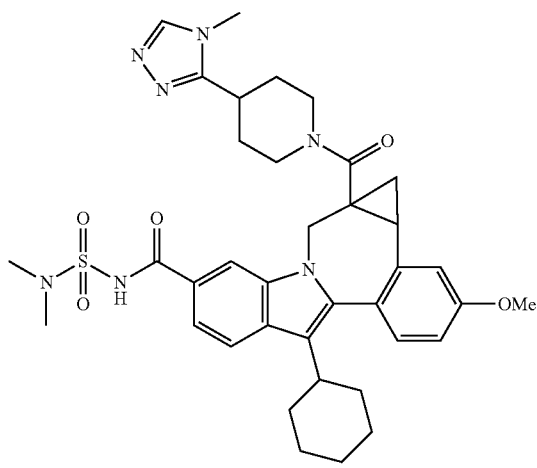
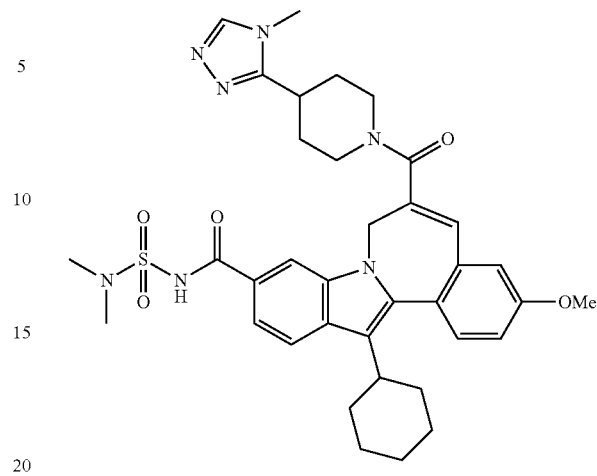

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(4-methyl-4H-1,2,4-triazol-3-yl)-1-piperidinyl]carbonyl]-, Prepared as a TFA salt from the coupling between the racemic acid and 4-(4-methyl-4H-1,2,4-triazol-3-yl)piperidine (2HCl, H2O) in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate 30 mL/min, Column: Xterra Prep MS C18 5u 30×50 mm, Fraction Collection: 9.23-9.83 min. (UV detection at 220 nm). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=700.46, HPLC R$_f$=1.707 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)$^+$=700.39, HPLC R$_f$=1.283 min. Analytical HPLC were performed by using Shimadzu-VP instrument with UV detection at 254 nm and 256 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 min, Stop time=20 min, Flow Rate=1 ml/min, Column: Waters Sunfire C-18, 4.6×150 mm, 3.5 um, R$_f$=8.49 min; Column: Waters Xbridge Phenyl column 4.6×150 mm, 3.5 um, R$_f$=8.37 mM.

7H-indolo[2,1-a][2]benzazepine-10-carboxamide, 13-cyclohexyl-N-[(dimethylamino)sulfonyl]-3-methoxy-6-[[4-(4-methyl-4H-1,2,4-triazol-3-yl)-1-piperidinyl]carbonyl]-. Prepared as a TFA salt from the coupling between the unsaturated acid and 4-(4-methyl-4H-1,2,4-triazol-3-yl)piperidine (2HCl, H2O) in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 9.34-9.94 min. (UV detection at 220 nm). $^1$H NMR (500 MHz, CD$_3$OD) δ 9.22 (s, 1H), 8.12 (s, 1H), 7.91 (d, J=9, 1H), 7.58 (dd, J=8.5, 1.5, 1H), 7.56 (d, J=9, 1H), 7.16 (dd, J=8.5, 2.5, 1H), 7.10 (d, J=2.5, 1H), 7.01 (s, 1H), 5.15 (broad m, 1H), 4.38 (broad m, 1H), 3.93 (s, 3H), 3.88 (s, 3H), 3.40-3.26 (m overlapping solvent peak, 2H), 3.14 (overlapping m, 2H), 3.02 (s, 6H), 2.88 (overlapping m, 2H), 2.21-1.88 (overlapping m, 6H), 1.79 (overlapping broad m, 4H), 1.45 (overlapping broad m, 3H), 1.24 (broad m, 1H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=686.43, HPLC R$_f$=1.688 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)$^+$=686.41, HPLC R$_f$=1.282 min. Analytical HPLC were performed by using Shimadzu-VP instrument with UV detection at 254 nm and 256 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 mM, Stop time=20 min, Flow Rate=1 ml/min, Column: Waters Sunfire C-18, 4.6×150 mm, 3.5 um, R$_f$=8.28 min; Column: Waters Xbridge Phenyl column 4.6×150 mm, 3.5 um, R$_f$=8.57 min.

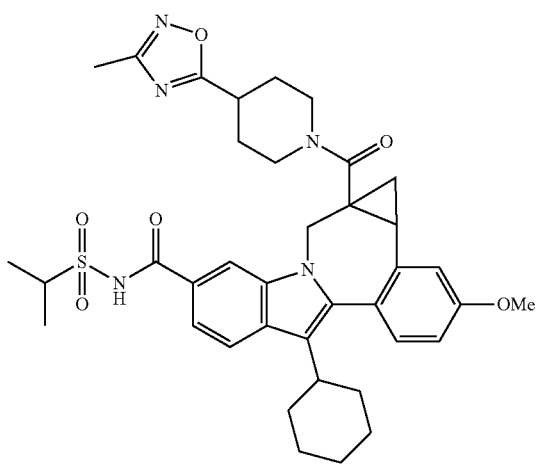

Cycloprop[d]indolo[2,1-a][2]benzazepine-5-carboxamide, 8-cyclohexyl-1,1a,2,12b-tetrahydro-11-methoxy-N-[(1-methylethyl)sulfonyl]-1a-[[4-(3-methyl-1,2,4-oxadiazol-5-yl)-1-piperidinyl]carbonyl]-. Prepared as a TFA salt from the coupling between the racemic acid, cycloprop[d]indolo[2,1-a][2]benzazepine-1a(2H)-carboxylic acid, 8-cyclohexyl-1,12b-dihydro-11-methoxy-5-[[[(1-methylethyl)sulfonyl]amino]carbonyl]- and 3-methyl-5-(piperidin-4-yl)-1,2,4-oxadiazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 9.35-9.95 min. (UV detection at 220 nm). $^1$H NMR (500 MHz, CD$_3$OD, as a mixture of two isomers in about 2.5:1 ratio) δ 8.12 (s, 0.4H), 7.97 (s, 1H), 7.91 (d, J=8.5, 0.4H), 7.85 (d, J=8.5, 1H), 7.63 (d, J=9.0, 0.4H), 7.53 (d, J=8.0, 1H), 7.32 (d, J=8.5, 0.4H), 7.31 (d, J=8.5, 1H), 7.19 (d, J=2.5, 1H), 7.18 (d, J=2.5, 0.4H), 7.02 (dd, J=8.5, 2.5, 1H), 7.00 (dd, 0.4H), 5.07 (broad d, J=15, 1H), 4.80 (d, 0.4H), 4.12 (d, J=15, 0.4H), 3.99 (m, 1.4H), 3.91 (s, 1.2H), 3.90 (s, 3H), 3.64 (d, J=15, 1H), 3.42-3.30 (overlapping m, 1.2H), 3.30-3.17 (m, 1H), 3.10 (broad m, 1H), 2.98 (m, 1.4H), 2.91-2.69 (overlapping m, 2.4H), 2.63 (broad m, 1H), 2.53 (dd, J=9.9, 6.3, 0.4H), 2.38 (s, 4.2H), 2.27-1.74 (overlapping m, 13H), 1.64 (broad d, 1.4H), 1.56-1.37 (overlapping m, 5.6H), 1.47-1.44 (s overlapping with m, 8.4H), 1.36-1.19 (overlapping m, 3H), 1.08 (dd, J=9.8, 6.0, 0.4H), 0.17 (t, J=6.0, 0.4H). LC/MS were performed by using Shimadzu-VP instrument with UV detection at 220 nm and Waters Micromass, HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=700.38, HPLC R$_t$=1.897 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)$^+$=700.45, HPLC R$_t$=1.265 min. Analytical HPLC were performed by using Shimadzu-VP instrument with UV detection at 254 nm and 256 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 min, Stop time=20 min, Flow Rate=1 ml/min, Column: Waters Sunfire C-18, 4.6×150 mm, 3.5 um, R$_t$=11.49 min; Column: Waters Xbridge Phenyl column 4.6×150 mm, 3.5 um, R$_t$=10.30 min.

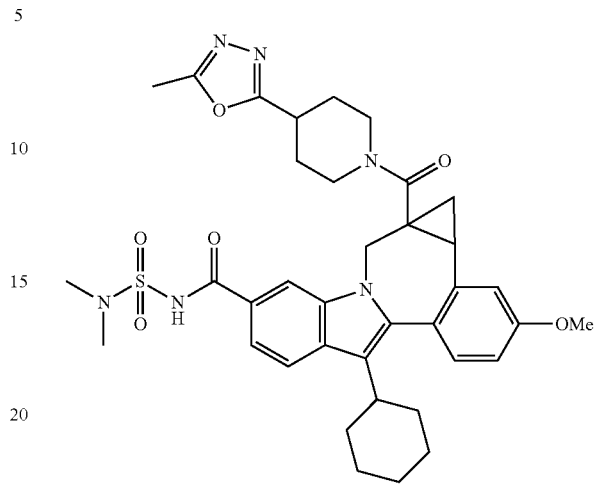

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(5-methyl-1,3,4-oxadiazol-2-A-1-piperidinyl]carbonyl]-, Prepared as a TFA salt from the coupling between the racemic acid and 2-methyl-5-(piperidin-4-yl)-1,3,4-oxadiazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 8.85-9.45 min. (UV detection at 220 nm). $^1$H NMR (500 MHz, CD$_3$OD, as a mixture of two isomers in about 2:1 ratio) δ 8.09 (s, 0.5H), 7.99 (s, 1H), 7.91 (d, J=8.5, 0.5H), 7.87 (d, J=8.5, 1H), 7.62 (dd, 0.5H), 7.55 (dd, 1H), 7.33 (d, J=8.5, 0.5H), 7.32 (d, J=8.5, 1H), 7.20 (d, J=2.5, 1H), 7.19 (d, J=2.5, 0.5H), 7.03 (dd, J=8.5, 2.5, 1H), 7.00 (dd, J=8.5, 2.5, 0.5H), 5.10 (broad d, J=15, 1H), 4.82 (d, 0.5H), 4.15 (d, J=15, 0.5H), 3.92 (s, 1.5H), 3.90 (s, 3H), 3.67 (d, J=15, 1H), 3.39-3.10 (overlapping m, 3H) 3.10-2.93 (overlapping in, 2.5H), 3.00 (s, 9H), 2.91-2.80 (overlapping m, 1.5H), 2.72 (broad m, 0.5H), 2.65 (broad m, 1H), 2.55 (s, 4.5H), 2.52 (m, 0.5H), 2.29-1.74 (broad overlapping m, 14H), 1.63 (broad d, 1.5H), 1.57-1.38 (broad overlapping m, 5.5H), 1.38-1.19 (broad overlapping m, 3.5H), 1.07 (dd, J=9.6, 6.0, 0.5H), 0.18 (t, J=6.0, 0.5H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=701.34, HPLC R$_t$=1.842 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=4 ml/min, Column: Phenomenex Lina C18 5 um 3.0×50 mm; (ES+) m/z (M+H)$^+$=701.40, HPLC R$_t$=1.315 min. Analytical HPLC were performed by using Shimadzu-VP instrument with UV detection at 254 nm and 256 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 min, Stop time=20 min, Flow Rate=1 ml/min, Column: Waters Sunfire C-18, 4.6×150 min, 3.5 um, $R_t$=10.78 min; Column: Waters Xbridge Phenyl column 4.6×150 mm, 3.5 um, $R_t$=9.65 min.

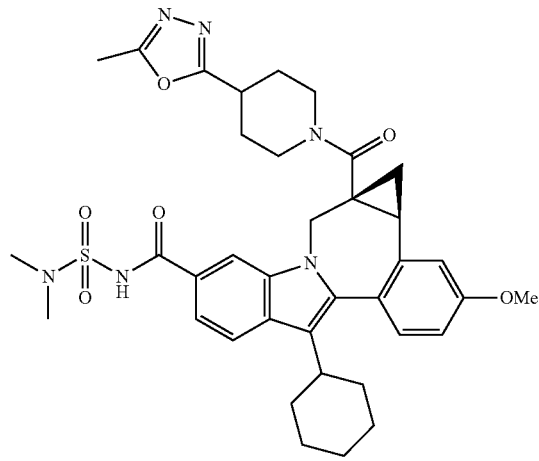

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(5-methyl-1,3,4-oxadiazol-2-yl)-1-piperidinyl]carbonyl]-, (1aR,12bS)-. Prepared as a TFA salt from the coupling between the chiral acid, cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (1aR,12bS)- and 2-methyl-5-(piperidin-4-yl)-1,3,4-oxadiazole in a similar manner as described above. Purification by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start %©B=30, Final % B=100, Gradient time 10 min, Stop time=12 min, Flow Rate=30 mL/min, Column: Xterra Prep MS C18 5u 30×50 mm, Fraction Collection: 8.85-9.45 mM. (UV detection at 220 nm). LC/MS were performed by using Shimadzu-VP instrument with UV detection at 220 inn and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Xterra MS C18 S7 3.0×50 mm; (ES+) m/z $(M+H)^+$=701.34, HPLC $R_t$=1.817 min. HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Stop time=3 min, Flow Rate=4 ml/min, Column: Phenomenex Lina C18 5 um 3.0×50 mm; (ES+) m/z $(M+H)^+$=701.34, HPLC $R_t$=1.345 min. Analytical HPLC method: Solvent A=5% MeOH-95% $H_2O$-10 mM $NH_4HCO_3$ (pH=9.5), Solvent B=95% MeOH-5% $H_2O$-10 mM $NH_4HCO_3$ (pH=9.5), Start % B=10, Final % B=100, Gradient time=10 min, Stop time 20 min, Flow Rate=1 ml/min, Column. Phenomenex Gemini, $R_t$=10.89 min; Column: Waters Xbridge Phe, $R_t$=10.42 min. Optical rotation [α]=−66.64, c=3.14 mg/ml (MeOH), 589 nm, 50 mm cell.

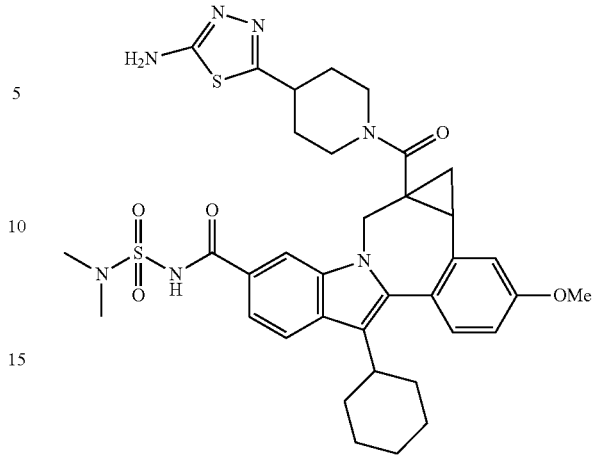

Cycloprop[d]indolo[2,1-a][2]benzazepine-5-carboxamide, 1a-[[4-(5-amino-1,3,4-thiadiazol-2-yl)-1-piperidinyl]carbonyl]-8-cyclohexyl-N-[(dimethylamino)sulfonyl]-1,1a,2,12b-tetrahydro-11-methoxy-. Prepared as a TFA salt from the coupling between the racemic acid and 5-(piperidin-4-yl)-1,3,4-thiadiazol-2-amine in a similar manner as described above. Purification by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 8.18-8.78 min. (UV detection at 220 nm). $^1$H NMR (500 MHz, $CD_3OD$, as a mixture of two isomers in about 2.5:1 ratio) 8.09 (s, 0.4H), 7.99 (s, 1H), 7.93 (d, J=8.5, 0.4H), 7.89 (d, J=8.5, 1H), 7.63 (d, J=7.0, 0.4H), 7.56 (d, J=8.5, 1H), 7.34 (d, J=8.5, 1.4H), 7.21 (d, J=2.5, 1H), 7.19 (d, J=2.5, 0.4H), 7.04 (dd, J=8.5, 2.5, 1H), 7.02 (dd, 0.4H), 5.14 (broad d, 1H), 4.94-4.83 (d overlapping with solvent peak, 0.4H), 4.17 (d, J=15, 0.4H), 3.92 (s, 1.2H), 3.91 (s, 3H), 3.70 (d, 15, 1H), 3.36-3.27 (overlapping m, 2.8H), 3.2 (overlapping m, 1.4H), 3.06-2.95 (overlapping m, 2H), 3.01 (s, 8.4H), 2.86 (broad m, 0.4H), 2.67 (broad m, 1.4H), 2.55 (dd, J=9.6, 6.3, 0.4H), 2.30-1.88 (broad overlapping m, 8H), 1.88-1.74 (broad overlapping m, 4H), 1.65 (broad d, 1H), 1.58-1.37 (broad overlapping m, 5H), 1.37-1.20 (broad overlapping m, 5H), 1.08 (dd, J=9.9, 6.0, 0.4H), 0.22 (t, J=6.0, 0.4H). LC/MS were performed by using Shimadzu-VP instrument with UV detection at 220 nm and Waters Micromass. HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Stop time=3 min, Flow Rate=5 ml/min, Column: Xterra MS C18 S7 3.0×50 mm; (ES+) ink $(M+H)^+$=718.28, HPLC $R_t$=1.715 min. HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Stop time=3 min, Flow Rate=4 ml/min, Column: Phenomenex Lina C18 5 um 3.0×50 mm; (ES+) m/z $(M+H)^+$=718.38, HPLC $R_t$=−1.210 min. Analytical HPLC were performed by using Shimadzu-VP instrument with UV detection at 254 nm and 256 nm. Analytical HPLC method: Solvent A=5% MeCN-95% $H_2O$-0.1% TFA, Solvent B=95% MeCN-5% $H_2O$-0.1% TFA, Start % B=10, Final % B=100, Gradient time=10 min, Stop time=20 min, Flow Rate=1 ml/min, Column: Waters Sunfire C-18, 4.6×150 mm, 3.5 um, $R_t$=8.80 min; Column: Waters Xbridge Phenyl column 4.6×150 mm, 3.5 um, $R_t$=8.52 min.

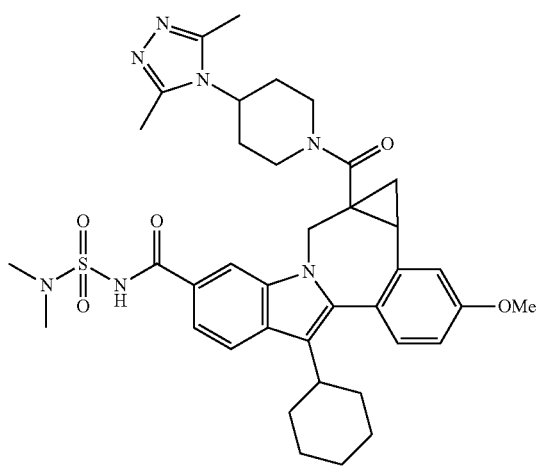
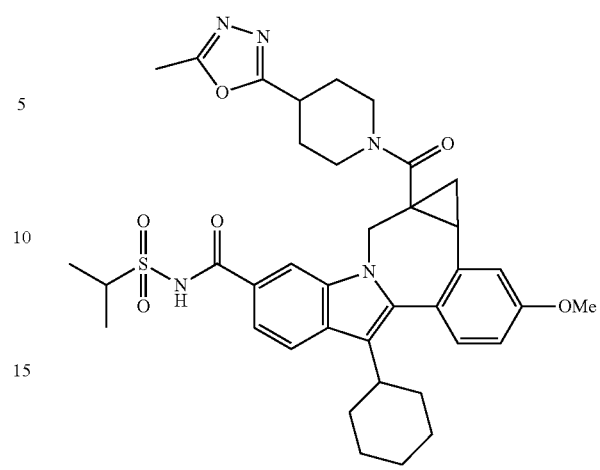

Cycloprop[d]indolo[2,1-a][2]benzazepine-5-carboxamide, 8-cyclohexyl-N-[(dimethylamino)sulfonyl]-1a-[[4-(3,5-dimethyl-4H-1,2,4-triazol-4-yl)-1-piperidinyl]carbonyl]-1,1a,2,12b-tetrahydro-11-methoxy-. Prepared as a TFA salt from the coupling between the racemic acid and 5-(piperidin-4-yl)-1,3,4-thiadiazol-2-amine in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min., Flow Rate=30 mL/min, Column: Xterra Prep MS C18 5u 30×50 mm, Fraction Collection: 7.59-8.19 min. (UV detection at 220 nm). $^1$H NMR (500 MHz, CD$_3$OD, as a mixture of two isomers in about 2:1 ratio) δ 8.03 (overlapping s, 1.5H), 7.93 (overlapping d, 1.5H), 7.59 (overlapping dd, 1.5H), 7.34 (d, J=8.5, 1.5H), 7.21 (overlapping m, 1.5H), 7.04 (dd, J=8.5, 2.5, 1H), 7.01 (dd, J=8.5, 2.5, 0.5H), 5.16 (d, J=15, 1H), 4.93 (d, 0.5H), 4.69 (m, 1H), 4.43 (m, 0.5H), 4.21 (d, J=15.5, 0.5H), 3.92 (s, 1.5H), 3.91 (s, 3H), 3.69 (d, J=15.5, 1H), 3.20 (m, 1H), 3.09-2.92 (m, 1H), 3.02 (s, 6H), 2.97 (s, 3H), 2.90-2.76 (s and overlapping m, 5.5H), 2.76-2.41 (broad s and overlapping m, 9H), 2.31 (broad in, 1.5H), 2.25-1.88 (broad overlapping m, 9H), 1.88 (broad m, 4H), 1.63 (broad d, 1H), 1.55-1.37 (broad overlapping m, 5.5H), 1.37-1.18 (broad overlapping m, 3.5H), 1.06 (broad m, 0.5H), 0.21 (t, J=6.1, 0.5H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=714.46, HPLC R$_t$=1.675 mM. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=4 ml/min, Column: Phenomenex Lina C18 5 um 3.0×50 mm; (ES+) m/z (M+H)$^+$=714.47, HPLC R$_t$=1.207 min. Analytical HPLC were performed by using Shimadzu-VP instrument with UV detection at 254 nm and 256 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 min, Stop time=20 min, Flow Rate=1 ml/min, Column: Waters Sunfire C-18, 4.6×150 mm, 3.5 um, R$_t$=7.65 min; Column: Waters)(bridge Phenyl column 4.6×150 mm, 3.5 um, R$_t$=8.31 mM.

Cycloprop[d]indolo[2,1-a][2]benzazepine-5-carboxamide, 8-cyclohexyl-1,1a,2,12b-tetrahydro-11-methoxy-N-[(1-methylethyl)sulfonyl]-1a-[[4-(5-methyl-1,3,4-oxadiazol-2-yl)-1-piperidinyl]carbonyl]-. Prepared as a TFA salt from the coupling between the racemic acid, cycloprop[d]indolo[2,1-a][2]benzazepine-1a(2H)-carboxylic acid, 8-cyclohexyl-1,12b-dihydro-11-methoxy-5-[[[(1-methylethyl)sulfonyl]amino]carbonyl]- and 2-methyl-5-(piperidin-4-yl)-1,3,4-oxadiazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 mM, Flow Rate=30 mL/min, Column: Xterra Prep MS C18 5u 30×50 mm, Fraction Collection: 8.68-9.91 min. (UV detection at 220 nm). $^1$H NMR (500 MHz, CD$_3$OD, as a mixture of two isomers in about 2:1 ratio) δ 8.10 (s, 0.5H), 7.99 (s, 1H), 7.92 (d, J=8.5, 0.5H), 7.87 (d, J=8.5, 1H), 7.63 (dd, J=8.5, 1.5, 0.5H), 7.56 (d, J=8.0, 1H), 7.31 (d, J=8.5, 1.5H), 7.19 (d, J=2.5, 1H), 7.18 (d, J=2.5, 0.5H), 7.02 (dd, J=8.5, 2.5, 1H), 6.99 (dd, 0.5H), 5.08 (broad d, J=14.7, 1H), 4.80 (d, J=14.7, 0.5H), 4.13 (d, J=15, 0.5H), 3.98 (m, 1.5H), 3.91 (s, 1.5H), 3.90 (s, 3H), 3.65 (d, J=15, 1H), 3.38-3.23 (overlapping m, 2H), 3.20 (m, 0.5H), 3.07 (broad m, 1H), 2.98 (m, 1.5H), 2.92-2.67 (overlapping m, 2.5H), 2.63 (broad m, 1H), 2.53 (m, 0.5H), 2.56 (s, 4.5H), 2.29-1.86 (overlapping m, 10H), 1.86-1.73 (overlapping in, 4H), 1.63 (broad d, 1.5H), 1.56-1.36 (overlapping m, 5H), 1.44 (broad s overlapping with m, 9H), 1.36-1.19 (overlapping m, 4H), 1.06 (dd, J=9.9, 6.0, 0.5H), 0.18 (t, J=6.0, 0.5H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=700.34, HPLC R$_t$=1.837 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=4 ml/min, Column: Phenomenex Lina C18 5 um 3.0×50 mm; (ES+) m/z (M+H)$^+$=700.46, HPLC R$_t$=1.207 min. Analytical HPLC were performed by using Shimadzu-VP instrument with UV detection at 254 nm and 256 nm. Analytical HPLC method: Solvent A=5% MeCN-95% H$_2$O-0.1% TFA, Solvent B=95% MeCN-5% H$_2$O-0.1% TFA, Start % B=10, Final % B=100, Gradient time=10 min, Stop time=20 min, Flow Rate=1 ml/min, Column: Waters Sunfire C-18, 4.6×150 mm, 3.5 um, R$_t$=10.67 min; Column: Waters Xbridge Phenyl column 4.6×150 mm, 3.5 um, R$_t$=9.61 min.

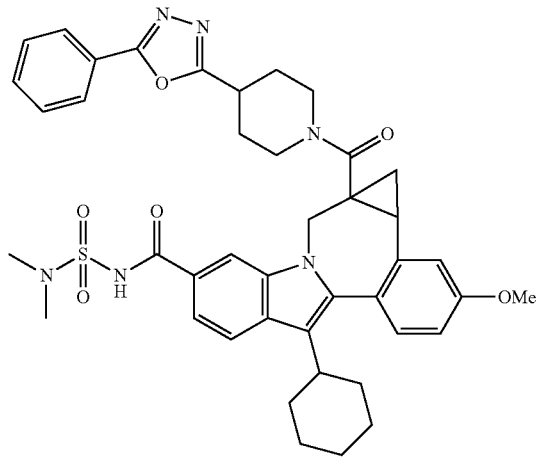

Cycloprop[d]indolo[2,1-a][2]benzazepine-5-carboxamide, 8-cyclohexyl-N-[dimethylamino)sulfonyl]-1,1a,2,12b-tetrahydro-11-methoxy-1a-[[4-(5-phenyl-1,3,4-oxadiazol-2-yl)-4-piperidinyl]carbonyl]-. Prepared as a TFA salt from the coupling between the racemic acid and 2-phenyl-5-(piperidin-4-yl)-1,3,4-oxadiazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 9.79-10.39 min. (UV detection at 220 nm). $^1$H NMR (500 MHz, CD$_3$OD, as a mixture of two isomers in about 2:1 ratio) δ 8.11 (s, 0.5H), 8.09-8.02 (overlapping in, 3H), 7.99 (s, 1H), 7.90 (d, J=8.6, 0.5H), 7.81 (broad s, 1H), 7.67-7.54 (overlapping m, 5H), 7.50 (broad d, 1H), 7.32 (d, J=8.5, 0.5H), 7.31 (d, J=8.5, 1H), 7.20 (overlapping d, 1.5H), 7.02 (dd, J=8.7, 2.5, 1H), 6.99 (dd, 0.5H), 5.10 (broad d, J=15, 1H), 4.84 (d, 0.5H), 4.14 (d, J=15, 0.5H), 3.91 (s, 1.5H), 3.90 (s, 3H), 3.66 (d, J=15, 1H), 3.43 (broad m, 1H), 3.39-3.30 (overlapping m, 1H), 3.29 (m, 0.5H), 3.20, 3.18, 3.14 (2 m overlapping with 1 broad m, 2H), 3.08-2.88 (overlapping m, 1.5H), 2.96 (broad s, 9H), 2.83 (overlapping m, 1.5H), 2.66 (broad m, 1H), 2.55 (dd, J=9.9, 6.3, 0.5H), 2.40-2.21 (broad overlapping m, 1.5H), 2.21-1.87 (broad overlapping in, 10H), 1.87-1.72 (broad overlapping m, 4H), 1.65 (broad d, 1H), 1.57-1.17 (overlapping m, 8H), 1.08 (dd, J=9.8, 6.0, 0.5H), 0.18 (t, J=6.0, 0.5H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=763.36, HPLC R$_t$=1.937 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 mM, Stop time=3 min, Flow Rate=4 ml/min, Column: Phenomenex Lina C18 5 um 3.0×50 mm; (ES+) m/z (M+H)$^+$=763.36, HPLC R$_t$=1.583 min. Analytical HPLC were performed by using Shimadzu-VP instrument with UV detection at 254 nm and 256 nm. Analytical HPLC method: Solvent A=5% MeOH-95% H$_2$O-10 mM NH$_4$HCO$_3$ (pH=9.5), Solvent B=95% MeOH-5% H$_2$O-10 mM NH$_4$HCO$_3$ (pH=9.5), Start % B=10, Final % B=100, Gradient time=10 min, Stop time=20 min, Flow Rate=1 ml/min, Column: Phenomenex Gemini, R$_t$=11.46 mM; Column: Waters Xbridge Phe, R$_t$=10.34 min.

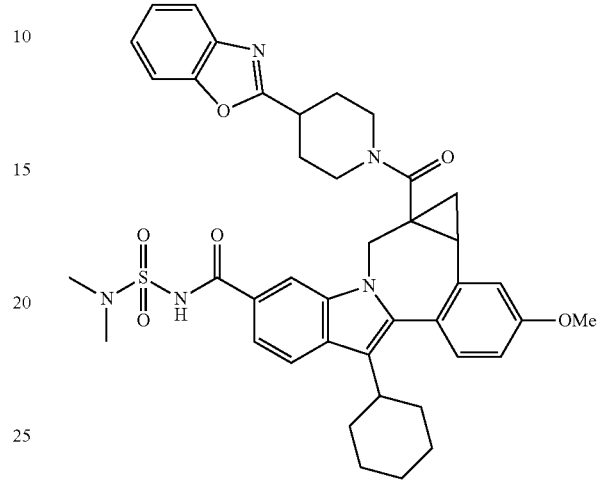

Cycloprop[d]indolo[2,1-a][2]benzazepine-5-carboxamide, 1a-[[4-(2-benzoxazolyl)-1-piperidinyl]carbonyl]-8-cyclohexyl-N-[(dimethylamino)sulfonyl]-1,1a,2,12b-tetrahydro-11-methoxy-. Prepared as a TFA salt from the coupling between the racemic acid and 2-(piperidin-4-yl)benzo[d]oxazole in a similar manner as described above. Purification by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=30, Final % B=100, Gradient time=10 min, Stop time=12 min, Flow Rate=30 mL/min, Column: Xterra Prep MS C18 5u 30×50 mm, Fraction Collection: 10.05-10.65 min. (UV detection at 220 nm). $^1$H NMR (500 MHz, CD$_3$OD, as a mixture of two isomers in about 2:1 ratio). δ 8.12 (s, 0.5H), 8.01 (s, 1H), 7.90 (d, J=8.5, 0.5H), 7.79 (broad s, 1H), 7.67-7.59 (overlapping m, 3.5H), 7.49 (broad d, 1H), 7.38 (overlapping m, 3H), 7.33 (d, 0.5H), 7.31 (d, J=8.5, 1H), 7.19 (overlapping d, 1.5H), 7.02 (dd, J=8.7, 2.5, 1H), 6.99 (dd, 0.5H), 5.11 (broad d, J=14.6, 1H), 4.84 (d, 0.5H), 4.14 (d, J=15, 0.5H), 3.91 (s, 1.5H), 3.90 (s, 3H), 3.66 (d, J=15, 1H), 3.40 (m, 0.5H), 3.37 (m, 0.5H), 3.20 (m, 0.5H), 3.14-3.03 (broad overlapping m, 2H), 3.03-2.90 (overlapping m, 1.5H), 2.96 (broad s, 9H), 2.84 (overlapping m, 2H), 2.66 (broad m, 1.5H), 2.54 (dd, J=9.9, 6.3, 0.5H), 2.37-2.21 (broad overlapping m, 1.5H), 2.21-1.86 (broad overlapping m, 9H), 1.86-1.70 (broad overlapping m, 4H), 1.61 (broad d, 1.5H), 1.56-1.17 (overlapping m, 8.5H), 1.08 (dd, J=9.8, 6.0, 0.5H), 0.18 (t, J=6.0, 0.5H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=736.35, HPLC R$_t$=1.978 min. HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Stop time=3 min, Flow Rate=4 ml/min, Column: Phenomenex Lina C18 5 um 3.0×50 mm; (ES+) m/z (M+H)⁺=736.41, HPLC $R_f$=1.622 min. Analytical HPLC were performed by using Shimadzu-VP instrument with UV detection at 254 nm and 256 nm. Analytical HPLC method: Solvent A=5% MeOH-95% H₂O-10 mM NH₄HCO₃ (pH=9.5), Solvent B=95% MeOH-5% H₂O-10 mM NH₄HCO₃ (pH=9.5), Start % B=10, Final % B=100, Gradient time=10 min, Stop time=20 min, Flow Rate=1 ml/min, Column: Phenomenex Gemini, $R_f$=11.47 min; Column: Waters Xbridge Phe, $R_f$=10.28 min.

The following table shows compounds that were prepared using similar chemistry to those described above and that were characterized using the following methods. Purification Method: Dionex LC; Chromeleon 6.70 sp1 LC software; HP 1100 quarternary pump for analytical; Varian prostar binary pump with 50 mL/min head for prep; Dionex UVD340U UV spectrometer; Sedex 75 ELS detector; Thermo-Finnigen MSQ Surveyor Plus mass spectrometer. LC Conditions: Column: Phenomenex Gemini 21.2×250 mm 5 um C18; Mobile Phase; A=Water; B=ACN; Modifier=0.1% TFA in A. Final Analysis Method: MassLynx 4.0 SP4 LC-MS software; CTC-Leap HTS-PAL autosampler; Agilent 1100 binary pump; Agilent 1100 photodiode array; Polymer Lab 2100 ELS detector (Evap. Temp.=45° C., Neb. Temp.=35° C.); Waters ZQ with ESCi mass spectrometer. LC Conditions: Column: Suppelco Ascentis C18 4.6×50 mm 2.7 micron; Mobile Phase: A=Water, 10 mM NH4OAc; B=CAN.

| Compound | Purity | Rt (min) |
|---|---|---|
| 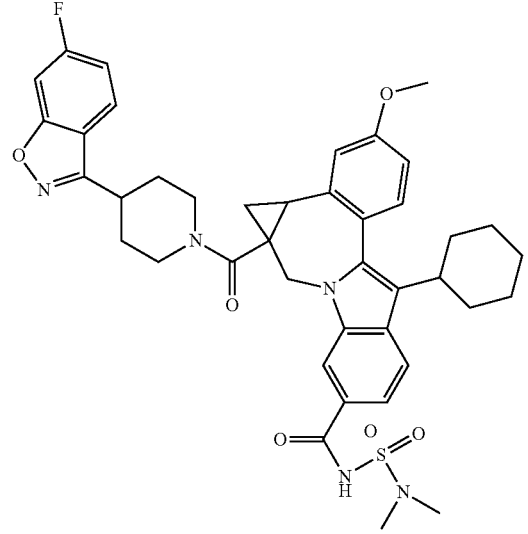 cycloprop[d]indolo[2,1-a][2]benzazepine-5-carboxamide, 8-cyclohexyl-N-[(dimethylamino)sulfonyl]-1a-[[4-(6-fluoro-1,2-benzisoxazol-3-yl)-1-piperidinyl]carbonyl]-1,1a,2,12b-tetrahydro-11-methoxy- | 95 | 3.78 |
| 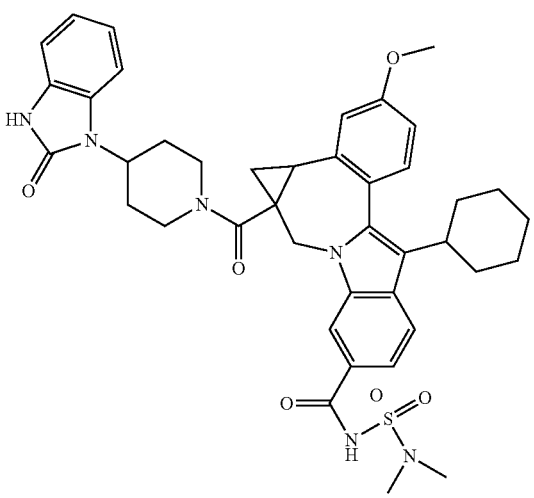 cycloprop[d]indolo[2,1-a][2]benzazepine-5-carboxamide, 8-cyclohexyl-1a-[[4-(2,3-dihydro-2-oxo-1H-benzimidazol-1-yl)-1-piperidinyl]carbonyl]-N-[(dimethylamino)sulfonyl]-1,1a,2,12b-tetrahydro-11-methoxy- | 100 | 3.06 |

-continued

| Compound | Purity | Rt (min) |
|---|---|---|
| cycloprop[d]indolo[2,1-a][2]benzazepine-5-carboxamide, 8-cyclohexyl-N-[(dimethylamino)sulfonyl]-1a-[[4-[3-(2-furanyl)-1H-pyrazol-5-yl]-1-piperidinyl]carbonyl]-1,1a,2,12b-tetrahydro-11-methoxy- | 95 | 3.28 |
| cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(5-methyl-1H-benzimidazol-2-yl)-1-piperidinyl]carbonyl]- | 100 | 3.21 |
| cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-[4-(4-methoxyphenyl)-1H-pyrazol-1-yl]-1-piperidinyl]carbonyl]- | 95 | 3.69 |

-continued

| Compound | Purity | Rt (min) |
|---|---|---|
| 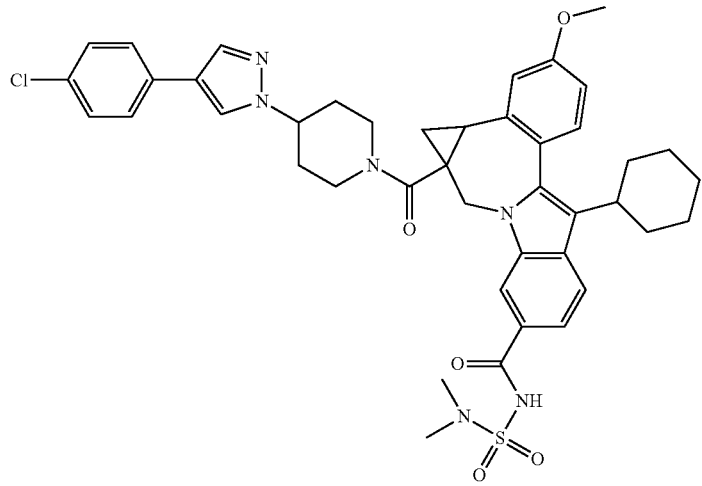 cycloprop[d]indolo[2,1-a][2]benzazepine-5-carboxamide, 1a-[[4-[4-(4-chlorophenyl)-1H-pyrazol-1-yl]-1-piperidinyl]carbonyl]-8-cyclohexyl-N-[(dimethylamino)sulfonyl]-1,1a,2,12b-tetrahydro-11-methoxy- | 95 | 4.06 |
| 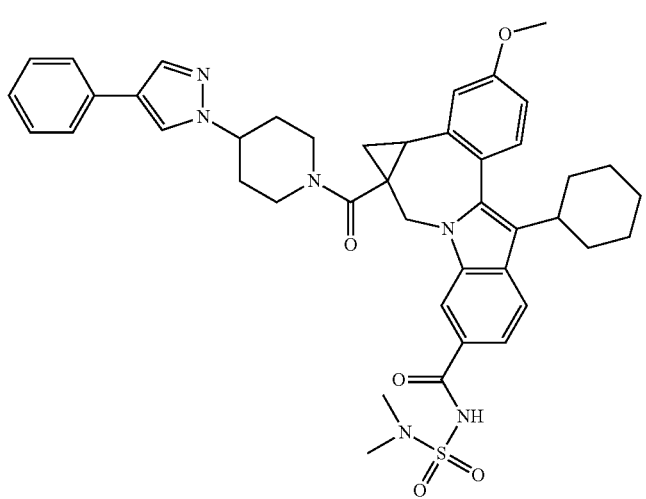 cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(4-phenyl-1H-pyrazol-1-yl)-1-piperidinyl]carbonyl]- | 95 | 3.79 |
| 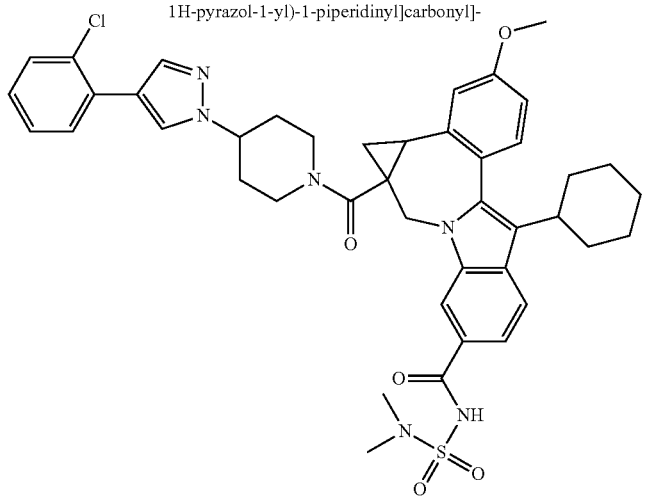 cycloprop[d]indolo[2,1-a][2]benzazepine-5-carboxamide, 1a-[[4-[4-(2-chlorophenyl)-1H-pyrazol-1-yl]-1-piperidinyl]carbonyl]-8-cyclohexyl-N-[(dimethylamino)sulfonyl]1,1a,2,12b-tetrahydro-11-methoxy- | 93.8 | 4 |

| Compound | Purity | Rt (min) |
|---|---|---|
| 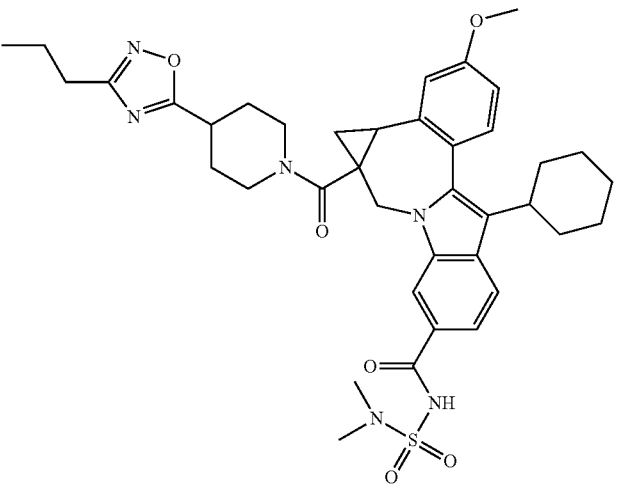<br>cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[4-(3-propyl-1,2,4-oxadiazol-5-yl)-1-piperidinyl]carbonyl]- | 95 | 3.72 |

The following compounds were prepared similarly as described above and were characterized using the following methods. Purification Method: Column: Phenomenex Gemini 21.2×250 mm 5 um C18, Guard column: Phenomenex Gemini 21.2×10 mm 5 um C18; Solvent A=5:95 MeCN:Water; Solvent B=95:5 MeCN:Water; Modifier=10 mM NH₄OAc; Flow rate=20 mL/min; % B=30 (0 to 5 min), 30 to 95 (5 to 23 min), 95 (23 to 27 min), 95 to 30 (27 to 27.5 min), 30 (27.5 to 30 min). Analytical Method: Waters ZQ with ESCi mass spectrometer; HPLC retention time was recorded in minutes; Solvent A=5:95 MeCN:Water; Solvent B=95:5 MeCN:Water; Modifier=10 mM NH₄OAc; Column: Supelco Ascentis 4.6×50 mm 2.7 um C18; Flow rate=2 mL/min; % B=10 to 95 (0 to 8 min), 95 (8 to 9 min), 95 to 10 (9 to 9.2 min), 10 (9.2 to 10 min, 3 mL/min).

| Compound | Purity (%) | Rt (min) | MH+ |
|---|---|---|---|
| 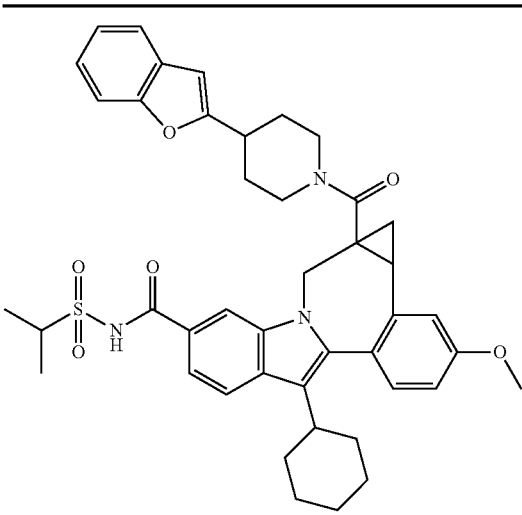<br>cycloprop[d]indolo[2,1-a][2]benzazepine-5-carboxamide, 1a-[[4-(2-benzofuranyl)-1-piperidinyl]carbonyl]-8-cyclohexyl-1,1a,2,12b-tetrahydro-11-methoxy-N-[(1-methylethyl)sulfonyl]- | 98.7 | 3.85 | 734.37 |

-continued

| Compound | Purity (%) | Rt (min) | MH+ |
|---|---|---|---|
| 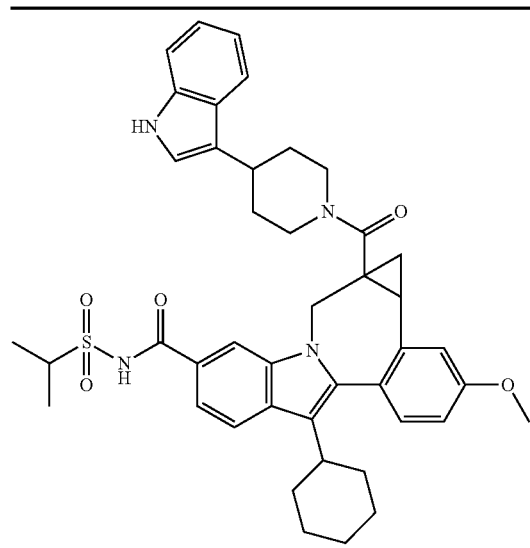 cycloprop[d]indolo[2,1-a][2]benzazepine-5-carboxamide, 8-cyclohexyl-1,1a,2,12b-tetrahydro-1a-[[4-(1H-indol-3-yl)-1-piperidinyl]carbonyl]-11-methoxy-N-[(1-methylethyl)sulfonyl]- | 96.1 | 3.47 | 733.37 |

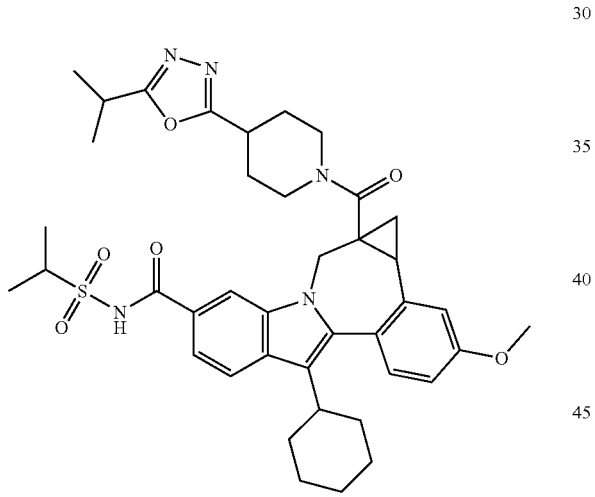

Cycloprop[d]indolo[2,1-a][2]benzazepine-5-carboxamide, 8-cyclohexyl-1,1a,2,12b-tetrahydro-11-methoxy-1a-[[4-[5-(1-methylethyl)-1,3,4-oxadiazol-2-yl]-1-piperidinyl]carbonyl]-N-[(1-methylethyl)sulfonyl]-. To a solution of the acid (35.1 mg, 0.053 mmol) in 1,2-dichloroethane (1 mL) at 0° C. was added 1,1'-carbonyldiimidazole (9.45 mg, 58.3 umol). After 30 min, isobutyrohydrazide (5.41 mg, 53 umol) was added. The coupling was allowed to proceed at 0° C. for 45 min, and then CBr$_4$ (35.2 mg, 106 umol) and Ph$_3$P (27.8 mg, 106 umol) were added in one portion. The mixture was stirred at room temperature overnight. The product was purified by preparation HPLC; MH+=728.7.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

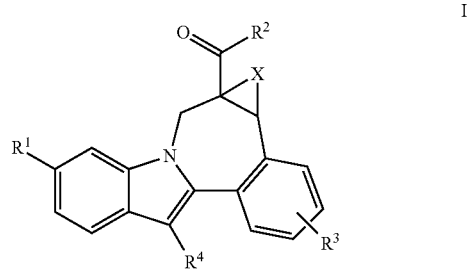

where:
$R^1$ is $CO_2R^5$ or $CONR^6R^7$;
$R^2$ is piperidine substituted with 1 $Ar^1$;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^8)(R^9)NSO_2$, or $(R^{10})SO_2$;
$R^7$ is hydrogen or alkyl;
$R^8$ is hydrogen or alkyl;
$R^9$ is hydrogen or alkyl;
$R^{10}$ is azetidinyl, pyrrolidinyl, piperidinyl, piperazinyl, N-(alkyl)piperazinyl, morpholinyl, thiomorpholinyl, homopiperidinyl, or homomorpholinyl;

Ar¹ is pyrrolyl, thienyl, furanyl, pyrazolyl, isoxazolyl, isothiazolyl, imidazolyl, oxazolyl, thiazolyl, oxadiazolyl, thiadiazolyl, indolyl, oxindolyl, benzofuranyl, benzothienyl, indazolyl, benzisoxazolyl, benzisothiazolyl, benzimidazolyl, benzimidazolonyl, benzoxazolyl, benzthiazolyl, or benztriazolyl, and is substituted with 0-2 substituents selected from halo, alkyl, cycloalkyl, alkoxy, amino, alkylamino, dialkylamino, carboxy, alkoxycarbonyl, furanyl, and phenyl where phenyl is substituted with 0-2 halo, alkyl, or alkoxy substituents; and X is absent, a bond, or methylene;

or a pharmaceutically acceptable salt thereof.

2. A compound of claim 1 where R¹ is CONR⁶R⁷; R² is piperidine substituted with 1 Ar¹; R³ is alkoxy; R⁴ is cycloalkyl; R⁶ is alkylSO₂ or (R⁸)(R⁹)NSO₂; R⁷ is hydrogen; R⁸ is alkyl; R⁹ is alkyl; Ar¹ is pyrazolyl, oxazolyl, thiazolyl, oxadiazolyl, thiadiazolyl, indolyl, benzofuranyl, benzisoxazolyl, benzimidazolyl, benzimidazolonyl, or benzoxazolyl, and is substituted with 0-2 substituents selected from halo, alkyl, amino, alkoxycarbonyl, furanyl, and phenyl where phenyl is substituted with 0-2 halo or alkoxy substituents; and X is a bond or methylene; or a pharmaceutically acceptable salt thereof.

3. A compound of claim 1 where R¹ is CONR⁶R⁷; R² is piperidine substituted with 1 Ar¹; R³ is methoxy; R⁴ is cyclohexyl; R⁶ is isopropylSO₂ or (dimethylamino)SO₂; R⁷ is:hydrogen; Ar¹ is (furanyl)pyrazolyl, thiazolyl, (methyl)oxadiazolyl, (ethyl)oxadiazolyl, (propyl)oxadiazolyl, (isopropyl)oxadiazolyl, (phenyl)oxadiazolyl, (amino)thiadiazolyl, indolyl, benzofuranyl, fluorobenzisoxazolyl, (methyl)benzimidazolyl, (phenyl)pyrazolyl, (chlorophenyl)pyrazolyl, (methoxyphenyl)pyrazolyl, benzimidazolonyl, or benzoxazolyl; and X is a bond or methylene; or a pharmaceutically acceptable salt thereof.

4. A compound of claim 1 where R¹ is CONR⁶R⁷; R⁶ is alkylSO₂, cycloalkylSO₂, haloalkylSO₂, (R⁸)(R⁹)NSO₂, or (R¹⁰)SO₂; and R⁷ is hydrogen.

5. A compound of claim 1 where R³ is hydrogen.

6. A compound of claim 1 where R³ is methoxy.

7. A compound of claim 1 where R⁴ is cyclohexyl.

8. A compound of claim 1 where R⁶ is (R⁸)(R⁹)NSO₂ or (R¹⁰)SO₂.

9. A compound of claim 1 where Ar¹ is pyrazolyl, thiazolyl, oxadiazolyl, thiadiazolyl, benzisoxazolyl, benzimidazolyl, benzimidazolonyl, or benzoxazolyl, and is substituted with 0-2 substituents selected from halo, alkyl, amino, alkylamino, dialkylamino, carboxy, alkoxycarbonyl, furanyl, and phenyl where phenyl is substituted with 0-2 halo, alkyl, or alkoxy substituents.

10. A compound of claim 1 where X is methylene.

11. A compound of claim 1 where X is a bond.

12. A compound of claim 1 according to the following stereochemistry

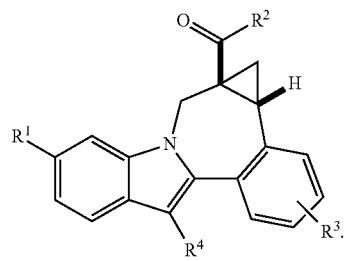

13. A compound of claim 1 selected from the group consisting of

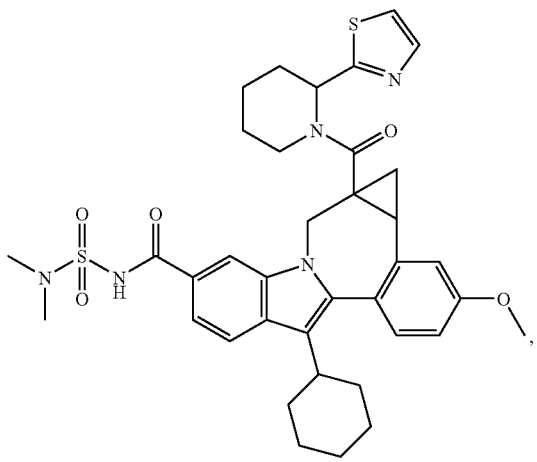

,

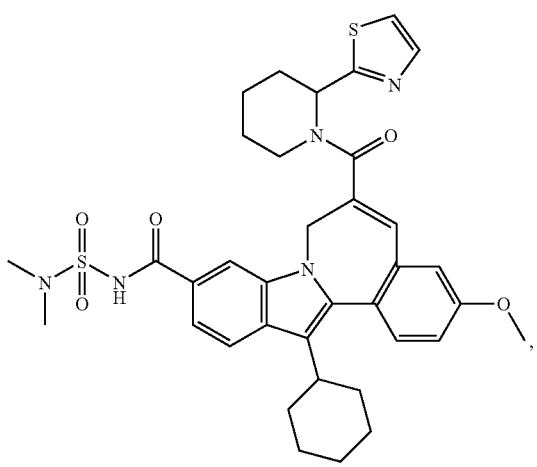

,

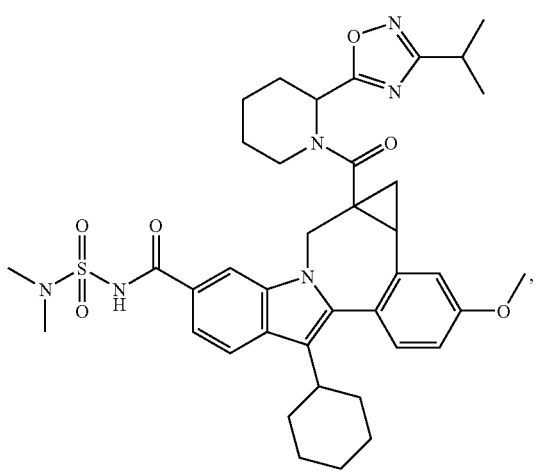

,

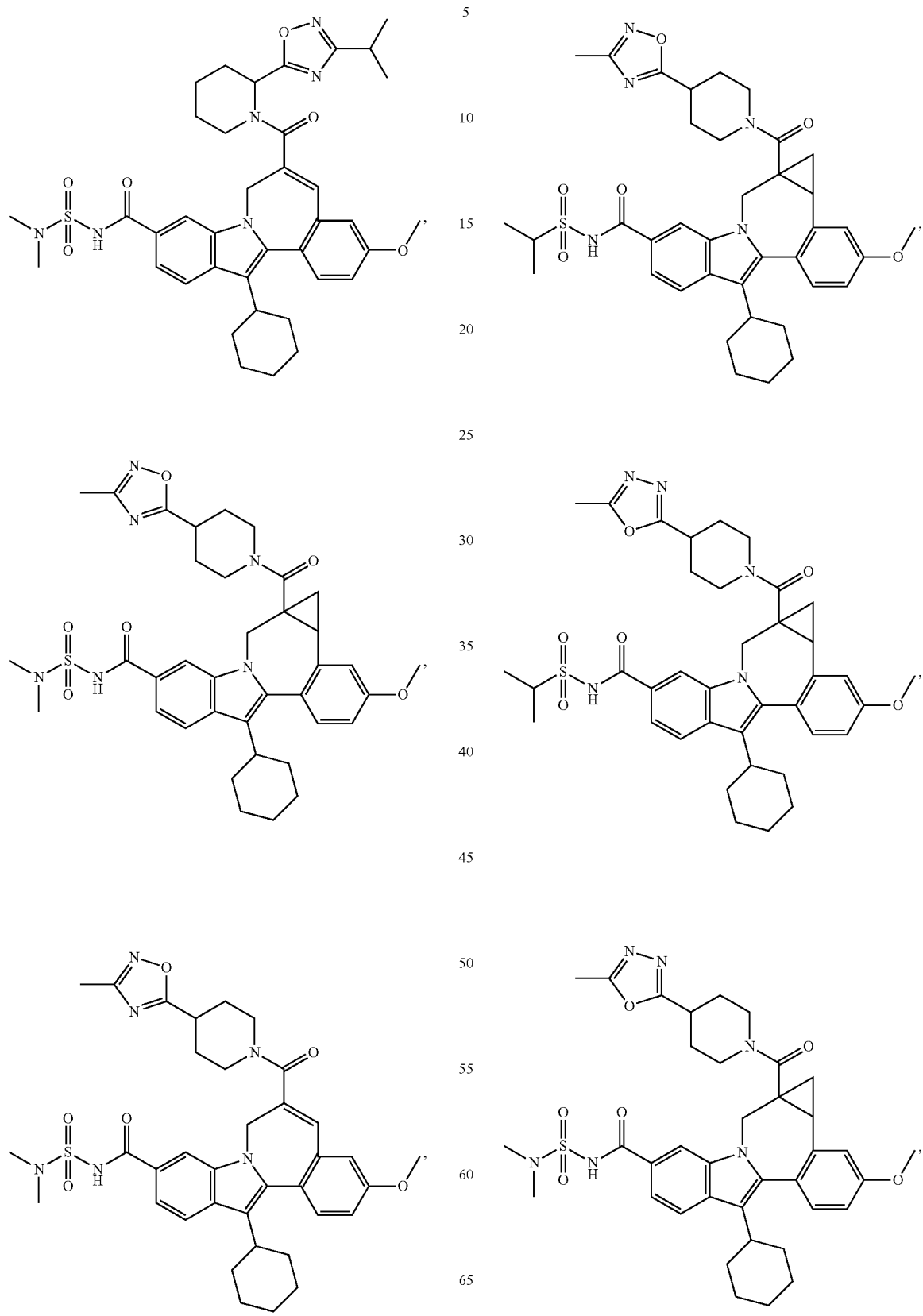

63
-continued
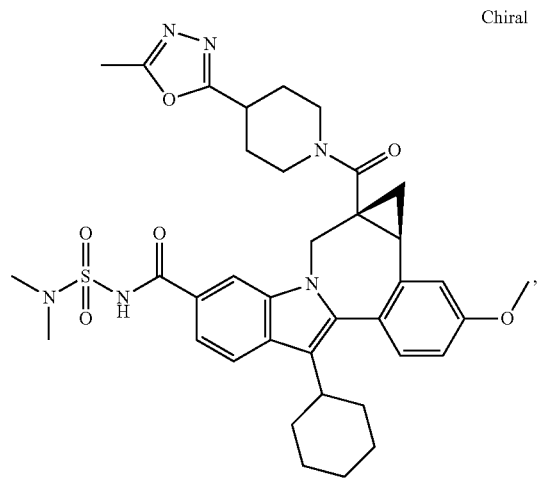
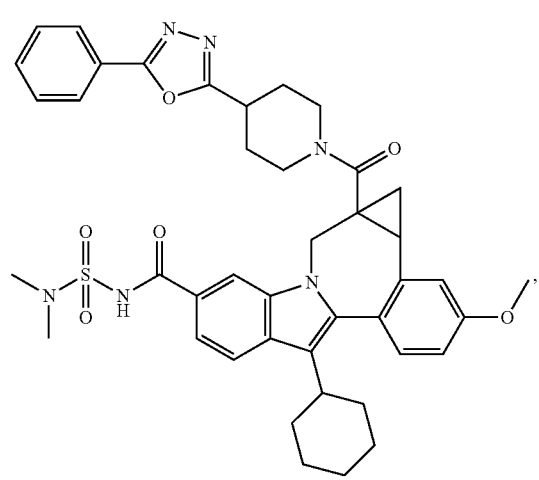
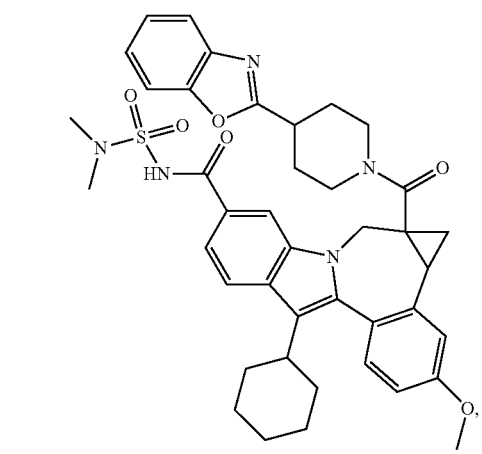
64
-continued
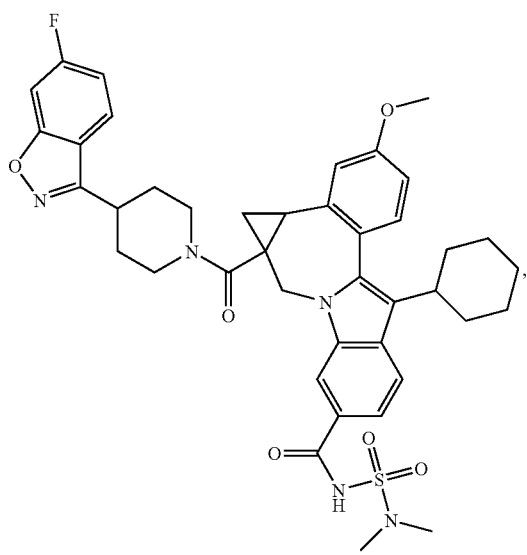
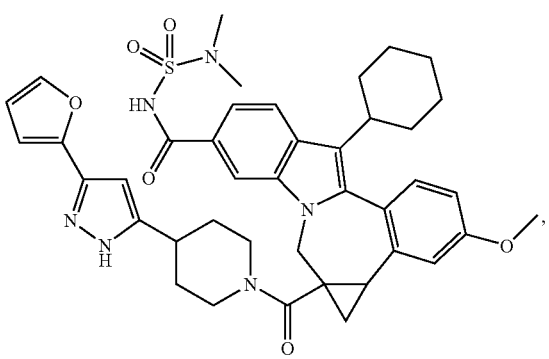

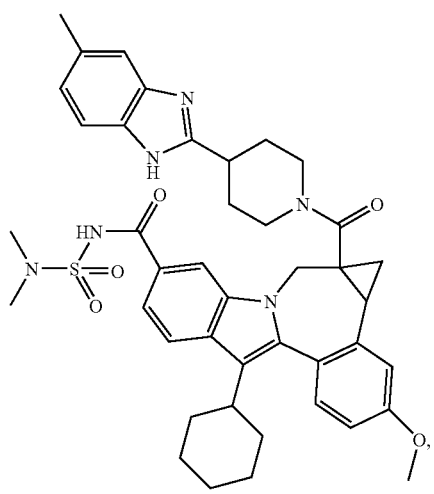
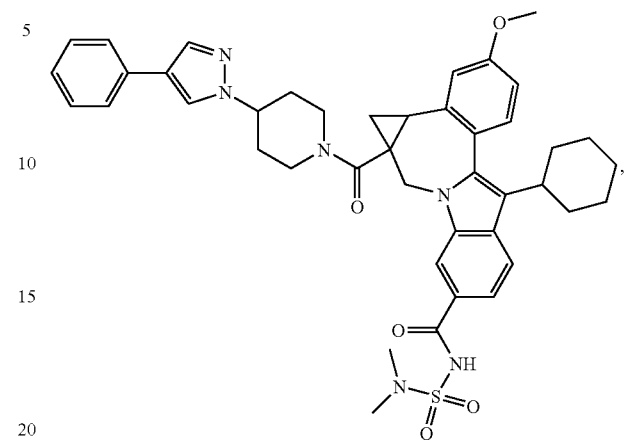
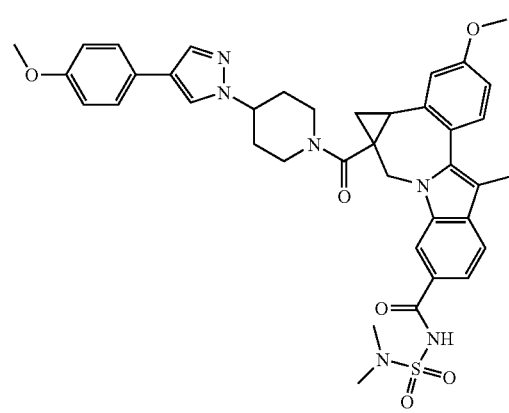
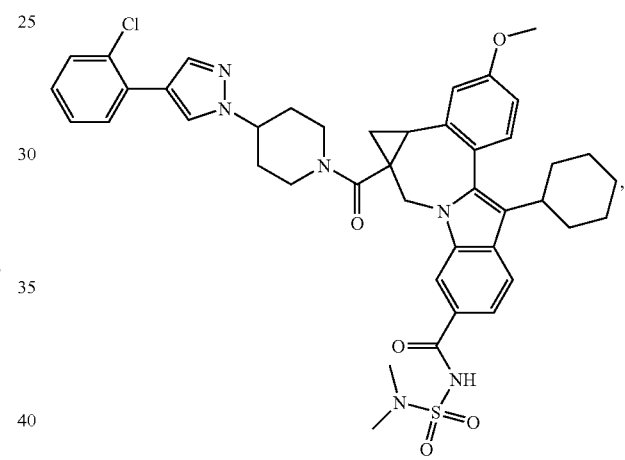
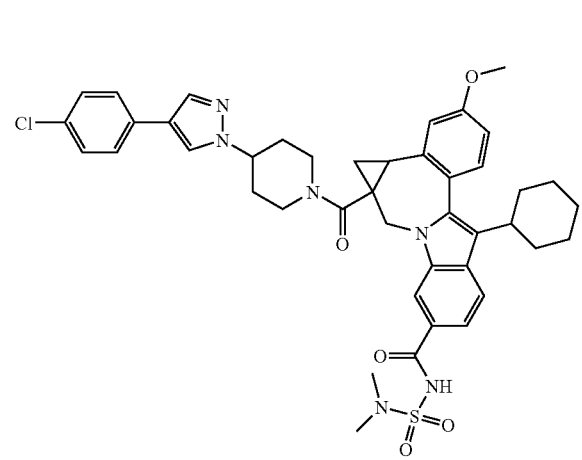
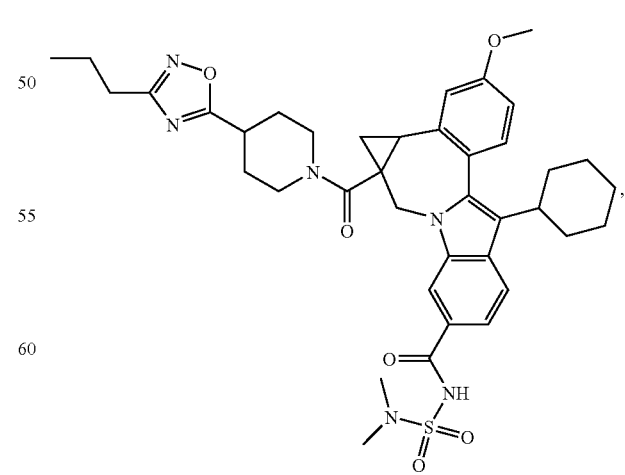

-continued
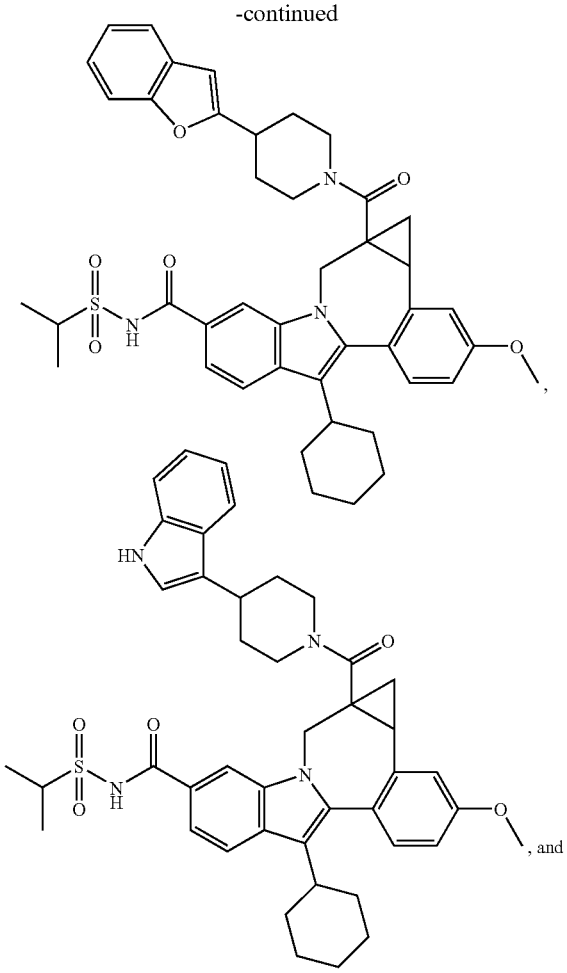
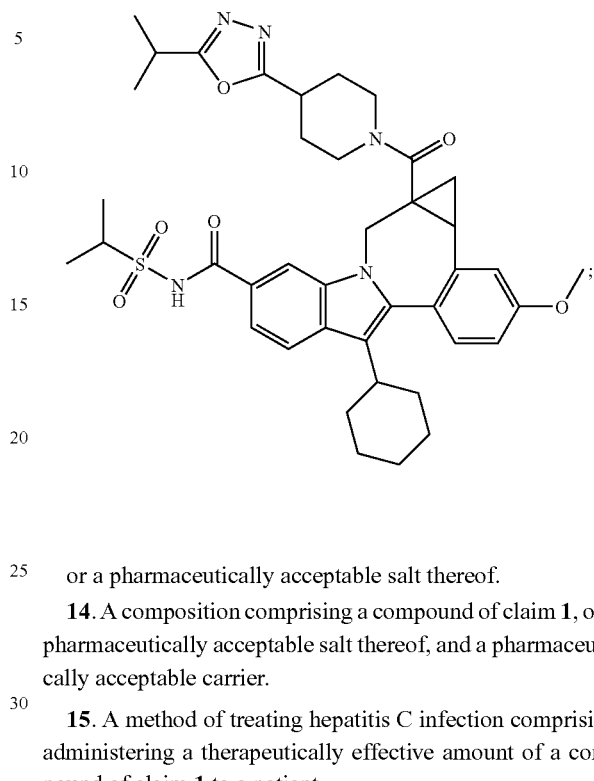
-continued
or a pharmaceutically acceptable salt thereof.
14. A composition comprising a compound of claim 1, or a pharmaceutically acceptable salt thereof, and a pharmaceutically acceptable carrier.
15. A method of treating hepatitis C infection comprising administering a therapeutically effective amount of a compound of claim 1 to a patient.
* * * * *

UNITED STATES PATENT AND TRADEMARK OFFICE
CERTIFICATE OF CORRECTION

PATENT NO. : 8,178,523 B2
APPLICATION NO. : 12/922722
DATED : May 15, 2012
INVENTOR(S) : Kap-Sun Yeung et al.

It is certified that error appears in the above-identified patent and that said Letters Patent is hereby corrected as shown below:

In the Claims:

Claim 1:

Column 58, line 61, change "or)($R^{10}$)$SO_2$;" to -- or ($R^{10}$)$SO_2$; --.

Claim 3:

Column 59, lines 27 and 28, change "is:hydrogen;" to -- is hydrogen; --.

Signed and Sealed this
Eleventh Day of March, 2014

Michelle K. Lee
*Deputy Director of the United States Patent and Trademark Office*